US009605066B2

(12) United States Patent
Osterroth et al.

(10) Patent No.: US 9,605,066 B2
(45) Date of Patent: *Mar. 28, 2017

(54) HUMANIZED ANTI-IL-10 ANTIBODIES FOR THE TREATMENT OF SYSTEMIC LUPUS ERYTHEMATOSUS (SLE)

(71) Applicant: BIOTEST AG, Dreieich (DE)

(72) Inventors: Frank Osterroth, Dietzenbach (DE); Christoph Uherek, Seligenstadt (DE); Christoph Bruecher, Eschborn (DE); Peter Röttgen, Ladenburg (DE); Benjamin Daelken, Frankfurt am Main (DE); André Engling, Bad Homburg (DE); Chantal Zuber, Frankfurt am Main (DE); Niklas Czeloth, Dreieich (DE); Andrea Wartenberg-Demand, Schrecksbach (DE); Marcus Gutscher, Langen (DE); Judith Wessels-Kranz, Frankfurt am Main (DE)

(73) Assignee: BIOTEST AG, Dreieich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/473,186

(22) Filed: Aug. 29, 2014

(65) Prior Publication Data
US 2015/0064179 A1 Mar. 5, 2015

Related U.S. Application Data

(62) Division of application No. 13/512,780, filed as application No. PCT/EP2010/068562 on Nov. 30, 2010, now Pat. No. 8,852,871.

(30) Foreign Application Priority Data

Nov. 30, 2009 (GB) .................................. 0920933.9
Nov. 30, 2009 (GB) .................................. 0920940.4
Nov. 30, 2009 (GB) .................................. 0920942.0

(51) Int. Cl.
A61K 39/00 (2006.01)
A61K 39/395 (2006.01)
C07K 16/00 (2006.01)
C07K 16/18 (2006.01)
C07K 16/22 (2006.01)
C07K 16/24 (2006.01)
C12N 1/21 (2006.01)
C12N 5/10 (2006.01)
C12N 15/00 (2006.01)
C12N 15/09 (2006.01)
C12N 15/11 (2006.01)
C12N 15/13 (2006.01)
C12N 15/63 (2006.01)
G01N 33/68 (2006.01)

(52) U.S. Cl.
CPC ....... *C07K 16/244* (2013.01); *G01N 33/6869* (2013.01); *A61K 2039/505* (2013.01); *C07K 2299/00* (2013.01); *C07K 2317/14* (2013.01); *C07K 2317/24* (2013.01); *C07K 2317/34* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,585,089 A | 12/1996 | Queen et al. |
| 5,776,451 A | 7/1998 | Hsu et al. |
| 5,837,232 A | 11/1998 | de Waal Malefyt et al. |
| 5,854,027 A | 12/1998 | Steipe et al. |
| 6,407,213 B1 | 6/2002 | Carter et al. |
| 8,647,622 B2 | 2/2014 | Lee et al. |
| 8,852,871 B2* | 10/2014 | Osterroth et al. ............. 435/7.1 |
| 8,956,607 B2* | 2/2015 | Osterroth et al. ......... 424/133.1 |
| 2005/0101770 A1 | 5/2005 | Presta |
| 2015/0064179 A1 | 3/2015 | Osterroth et al. |

FOREIGN PATENT DOCUMENTS

| DE | 19529026 | 1/1997 |
| EP | 0541214 | 5/1993 |
| JP | 09-508286 A | 8/1997 |
| RU | 2326127 | 3/2006 |
| WO | 2004/056312 | 8/2004 |
| WO | 2005/047326 | 5/2005 |
| WO | 2009/032661 | 3/2009 |

OTHER PUBLICATIONS

Llorente et al., 1993, Eur. Cytokine Netw. 4:421-430.*
Emilie, D. "Interleukin 10 in Disseminated Lupus Erythematosus", J. Soc. Biol., (2002); 196(1): 19-21.
Roskos, L. et al., "Human Antigolbulin Responses", in Measuring Immunity, M. T. Lotze and A. W. Thomson, eds. (2005); 172-186.
Roskos, L. et al., "The Clinical Pharmacology of Therapeutic Monoclonal Antibodies", Drug Dev. Res., (2004); 61: 108-120.
Tabrizi, M. and Roskos, L., "Preclinical and clinical safety of monoclonal antibodies", Drug. Discov. Today, (2007); 12: 540-547.
Hwang et al., "Use of human germline genes in a CDR homology-based approach to antibody humanization", Methods, 2005, vol. 36, pp. 35-42.

(Continued)

Primary Examiner — Elizabeth C Kemmerer
(74) Attorney, Agent, or Firm — LeClair Ryan, a Professional Corporation; Robin L. Teskin

(57) ABSTRACT

Provided is a humanized or chimeric antibody or fragment thereof capable of binding to interleukin-10 (IL-10), wherein said antibody or fragment thereof is capable of being administered to a subject in the absence of an intolerable increase in the level of pro-inflammatory cytokines. Further provided are methods of treatment involving the use of the antibody or fragment thereof.

14 Claims, 15 Drawing Sheets

(56) References Cited

OTHER PUBLICATIONS

Queen et al., "A humanized antibody that binds to the interleukin 2 receptor", Proc. Natl. Acad. Sci. USA, 1989, vol. 86, pp. 10029-10033.
Tsurushita et al., "Design of humanized antibodies: From anti-Tac to Zenapax", Methods, 2005, vol. 36, pp. 69-83.
Al-Janadi et al, (1996) J. of Clin. Immunol.; 16(4): 198-207.
Asadullah et al., (2003) Pharmacol. Rev. June; 55(2): 241-69.
"Biotest: Half Year Report as of Jun. 30, 2006." (2006).
Biotest Group Company Presentation: BT-063 A new treatment For SLE—Jun. 2008.
Biotext AG (2009) "Biotest AG: Clinical Development of BT-063 Started."
Capper et al., Clin. Exp. Immunol. Nov. 2004; 138(2): 348-56.
Carbonneil, C. et al., J. Immunol., 2004; 172: 7832-7840.
Carbonneil, C. et al., Int. Immunol., 2004; 16: 1037-1052.
Casali et al., (1987) Science. Apr. 3; 236(4797): 77-81.
Casset et al., "A peptide mimetic of an anti-CD4 monoclonal antibody by rational design", Biochem Biophys Res Comm. 2003; 307: 198-205.
Chen et al., "Selection and analysis of an optimized anti-VEGF antibody: crytstal structure of an affinity-matured Fab in complex with antigen", J Mol Biol. 1999; 293: 865-881.
Chun et al., J. Clin. Immunol. Sep. 2007; 27(5): 461-6.
Coleman, 1994, Research in Immunology, 145: 33-36.
de Waal Malefyt et al., (1991) J. Exp. Med. 174: 1209-1220.
Diaclone catalogue; IL-10 Antibody: B-N10 PE conjugated (Oct. 2008).
Hahn BH. Systemic Lupus Erythematosus. In: Kasper DL, Braunwald E, Fauci AS Hauser SL, Longo DL, Jameson JL, editors. In: Harrison's Principles of Internal Medicine (16th edition), New York (US): McGraw-Hill; 2005. pp. 1960-1967.
Hashimoto et al., (2001) J. Immunol. 167(7): 3619-25.
Holm et al., "Functional mapping and single chain construction of the anti-cytokeratin 8 monoclonal antibody TS1", Mol Immunol, 2007; 44(6): 1075-1084.
Honegger and Pluckthun (2001) J. Mol. Biol., 309: 657-670.
Honegger, A., "Aho's Amazing Atlas of Antibody Anatomy", www.bioc.uzh.ch/antibody, Mar. 19, 2008.
Howard et al., (1992) J. Clin. Immunol. 12(4): 239-47.
Huhn et al., (1996) Blood Jan. 15: 87(2): 699-705.
Isaacs et al., (2001) Arthritis Rheum. 44(9): 1998-2008.
Josephson et al., (2002) Structure 10; 981-987.
Josephson et al., (2000) J. Biol. Chem. 275(18): 13552-13557.
Liu and Jones (1998) Cytokine 10(2): 140-147.
Liu and Jones (1998) Cytokine 10(2): 148-153.
Liu et al., (2008) Immunological Reviews 222: 9-27.
Llorente et al., (1993) Eur. Cytokine Netw. Nov.-Dec.; 4(6): 421-7.
Llorente et al., (1995) J. Exp. Med. 181: 839-844.
Llorente et al., (2000) Arthritis & Rheumatism 43(8): 1790-1800.
MacCallum et al., "Antibody-antigen interactions: contact analysis and binding site topography", J Mol Biol. 1996 262: 732-745.
Midgley et al., (2009) Arthritis Rheum. 60(8): 2390-401.
Moreau et al., (1996) Brain 119 (Pt 1): 225-37.
Moreau et al., (2006) Bioinformatics 22(9): 1088-1095.
Paul, Fundamental Immunology, 3rd Edition, 1993, pp. 292-295, under the heading "Fv Structure and Diversity in Three Dimensions".
Park et al., Clin. Exp. Rheumatol. May-Jun. 1998; 16(3): 283-8.
Pletnev et al., (2005) BMC Structural Biology, Jun. 28; 5:10.
Podchernyaeva, N.S. et al., "Systemic Lupus Erythematosus", Pediatric Pharmacology, 2006 vol. 3, N6; pp. 21-28 (English Translation).
Ravirajan et al., (2004) Rheumatology 43: 442-447.
Reineke et al., (1998) Protein Science 7: 951-960.
Reineke et al., (1999) Nature Biotechnology 17(3): 271-275.
Rudikoff et al., Proc. Natl. Acad. Sci. USA, 79(6): 1979-1983, Mar. 1982.
Rules Based Medicine: Mean Values for 78 Analytes Aug. 2008.
Rutella S. et al., 2002; Blood, 100(7) 2562-2571.
Sabat et al., (1996) Molecular Immunology 33(4): 1103-11.
Sanz and Lee (2010) Nat. Rev. Rheumatol. 6: 326-337.
Schultz "Biotest Autumn Conference for Journalists and Analysts", (2004).
Strand et al., (2007) Nat. Rev. Drug Discovery 6: 75-92.
Tucci et al., Clin. & Exp. Immunol. (2008); 154:247-254.
Vajdos et al., "Comprehensive functional maps of the antigen-binding site of an anti-ErbB2 antibody obtained with shotgun scanning mutagenesis", J Mol Biol. 2002; 320(2): 415-428.
Vargas-Rojas, MI et al., Lupus, 2008; 17(4); 289-294.
Waibler et al., J. Allergy Clin. Immunol. (2008) 122(5): 890-2.
Weiss L. et al., Blood, 2004; 104: 3249-3256.
Welfle et al., (2001) Journal of Molecular Recognition 14: 89-98.
Wing et al., (1996) J. Clin. Invest. 98(12); 2819-26.
Winkler et al., (1999) Blood 94(7): 2217-24.
Zdanov et al., (1995) Structure vol. 3, pp. 591-601.
A.A. Yarilin, Foundations of Immunology: a textbook. Moscow, "Medicine", 1999, 608 pages; p. 171, second paragraph, pp. 172-173.
Robak & Robak (2009) Current Drug Targets; 10: 26-37.
Unknown, "Dictionary of Immunology (Menekigaku-Jiten), (2001), Second Edition, First Copy," entries for "H chain" and "H chain variable region" on p. 92; "L chain" on p. 112; "L-chain variable region" on p. 113; "variable region" on p. 135; and "complementarity determining regions" on p. 384.

* cited by examiner

```
          10        20        30        40        50        60
          |         |         |         |         |         |
DVLMTQTPLSLPVSLGDQASISCRSSQNIVHSNGNTYLEWYLQKPGQSPKLLIYKVSNRF
                      LCDR1                            LCDR2
          70        80        90        100       110
          |         |         |         |         |
SGVPDRFSGSGSGTDFTLKITRLEAEDLGVYYCFQGSHVPWTFGGGTKLEIKRA
                                 LCDR3
```

FIGURE 1A

```
          10        20        30        40        50        60
          |         |         |         |         |         |
QVQLKQSGPGLLQPSQSLSISCTVSGFSLATYGVHWVRQSPGKGLEWLGVIWRGGSTDYS
                              HCDR1                   HCDR2
          70        80        90        100       110
          |         |         |         |         |
AAFMSRLSITKDNSKSQVFFKMNSLQADDTAIYFCAKQAYGHYMDYWGQGTSVTVS
                                   HCDR3
```

GATGTTTTGATGACCCAAACTCCACTCTCCCTGCCTGTCAGTCTTGGAGATCAAGCCTCC
ATCTCTTGCAGATCTAGTCAGAACATTGTACATAGTAATGGAAACACCTATTTAGAATGG
TACCTGCAGAAACCAGGCCAGTCTCCAAAGCTCCTGATCTACAAAGTTTCCAACCGATTT
TCTGGGGTCCCAGACAGGTTCAGTGGCAGTGGATCAGGGACAGATTTCACACTCAAGATC
ACCAGATTGGAGGCTGAGGATCTGGGAGTTTATTACTGCTTTCAAGGTTCACATGTTCCG
TGGACGTTCGGTGGAGGCACCAAGCTGGAAATCAAACGGGCC

CAGGTGCAGCTGAAGCAGTCAGGACCTGGCCTACTGCAGCCCTCACAGAGCCTGTCCATA
TCCTGCACAGTCTCTGGTTTCTCATTAGCTACCTATGGTGTACACTGGGTTCGCCAGTCT
CCAGGAAAGGGTCTGGAGTGGCTGGGAGTGATTTGGAGAGGTGGGAGCACAGACTACACT
GCAGCTTTCATGTCCAGACTGAGCATCACCAAGGACAACTCCAAGAGCCAAGTTTTCTTT
AAAATGAACAGTCTGCAAGCTGATGACACTGCCATTTACTTCTGTGCCAAACAGGCGTAT
GGTCACTACATGGACTACTGGGGTCAAGGAACCTCAGTCACCGTCTCC

FIGURE 2B

Humanized VL variants

```
mVL    DVLMTQTPLSLPVSLGDQASISC RSSQNIVHSNGNTYLE WYLQKPGQSPKLLIY KVSNRFS GVPDRFSGSGSGTDFTLKITRLEAEDLGVYYC FQGSHVPWT FGGGTKLEIK
A17    DVVMTQSPLSLPVTLGQPASISC RSSQSLVYSDGNTYLN WFQQRPGQSPRRLIY KVSNRDS GVPDRFSGSGSGTDFTLKISRVEAEDVGVYYC MQGTHWP..
JK1                                                                                                              ..WT FGQGTKVEIK hVL1   DVVMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL2   DVLMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL3   DVVMTQTPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL4   DVVMTQSPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGGGTKVEIK
hVL5   DVVMTQSPLSLPVTLGQPASISC RSSQNIVHSNGNTYLE WFQQRPGQSPRRLIY KVENRFS GVPDRFSGSGSGTDFTLKISRVEAEDVGVYYC FQGSHVPWT FGGGTKVEIK
hVL6   DVVMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGGGTKVEIK
hVL7   DVVMTQSPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGQGTKVEIK
hVL8   DVLMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGGGTKVEIK
hVL9   DVVMTQSPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGGGTKVEIK
hVL10  DVVMTQSPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGGGTKVEIK
hVL11  DVVMTQTPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGGGTKVEIK
hVL12  DVVMTQTPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGQGTKVEIK
```

FIGURE 3

Humanized VH variants

```
mVH    QVQLKQSGPGLLQPSQLSLSCTVSGFSLA TYGVH WVRQSPGKGLEWLG VIWRGGSTDYSAAFMS RLSITKDNSKSQVFKMNSLQADDTAIYFCAK QAYGHYMDY WGQGTSVTVSS
3-66   EVQLVESGGGLVQPGGSLRLSCAASGFTVS SNYMS WVRQAPGKGLEWVS VIYSGGSTYYADSVKG RFTISRDNSKNTLYLQMNSLRAEDTAVYYCAR
*04
JH4                                                                                                                    ..YFDY WGQGTLVTVSS
hVH1   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH2   EVQLVESGGGLVQPGGSLRLSCAASGFSFA TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH3   EVQLVESGGGLVQPGGSLRLSCAASGFTFS TYGVH WVRQSPGKGLEWVS VIWRGGSTDYSAAFMS RFTISRDNSKNTLYLQMNSLRAEDTAVYYCAR QAYGHYMDY WGQGTLVTVSS
hVH4   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH5   EVQLVESGGGLVQPGGSLRLSCAASGFTFS TYGVH WVRQAPGKGLEWVS VIWRGGSTDYSAAFMS RLTISRDNSKNTLYLQMNSLRAEDTAVYYCAR QAYGHYMDY WGQGTLVTVSS
hVH6   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH7   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH8   EVQLVESGGGLVQPGGSLRLSCAASGFTFS TYGVH WVRQAPGKGLEWVS VIWRGGSTDYSAAFMS RFTISRDNSKNTLYFQMNSLRAEDTAVYYCAR QAYGHYMDY WGQGTLVTVSS
hVH9   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYFCAK QAYGHYMDY WGQGTLVTVSS
hVH10  EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAK QAYGHYMDY WGQGTLVTVSS
hVH11  EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTSVTVSS
hVH12  EVQLVESGGGLVQPGGSLRLSCAASGFTFS TYGVH WVRQAPGKGLEWLG VIWRGGSTDYSAAFMS RLTISRDNSKNTLYLQMNSLRAEDTAVYYCAR QAYGHYMDY WGQGTLVTVSS
```

FIGURE 3 (continued)

| | | | | | | |
|---|---|---|---|---|---|---|
| hVH13 | EVQLVESGGGLVQPGGSLRLSCAASGFTFS | TYGVH | WVRQAPGKGLEWVS | VIWRGGSTDYSAAFMS | RFTISRDNSKNTVFFQMNSLRAEDTAVYYCAR | QAYGHYMDY WGQGTLVTVSS |
| hVH14 | EVQLVESGGGLVQPGGSLRLSCAASGFSFA | TYGVH | WVRQSPGKGLEWVS | VIWRGGSTDYSAAFMS | RFTISRDNSKNTLYLQMNSLRAEDTAVYFCAK | QAYGHYMDY WGQGTLVTVSS |
| hVH15 | EVQLVESGGGLVQPGGSLRLSCAASGFTFS | TYGVH | WVRQSPGKGLEWLG | VIWRGGSTDYSAAFMS | RFTISRDNSKNTLYLQMNSLRAEDTAVYFCAK | QAYGHYMDY WGQGTSVTVSS |
| hVH16 | EVQLVESGGGLVQPGGSLRLSCAASGFTFS | TYGVH | WVRQAPGKGLEWLG | VIWRGGSTDYSAAFMS | RFTISRDNSKNTLYFQMNSLRAEDTAVYFCAK | QAYGHYMDY WGQGTSVTVSS |
| hVH17 | EVQLVESGGGLVQPGGSLRLSCAASGFTFS | TYGVH | WVRQAPGKGLEWLG | VIWRGGSTDYSAAFMS | RFTISRDNSKNTLYLQMNSLRAEDTAVYYCAK | QAYGHYMDY WGQGTSVTVSS |
| hVH18 | EVQLVESGGGLVQPGGSLRLSCAASGFSFA | TYGVH | WVRQSPGKGLEWLG | VIWRGGSTDYSAAFMS | RLTISKDNSKNTLYLQMNSLRAEDTAVYYCAR | QAYGHYMDY WGQGTLVTVSS |
| hVH19 | EVQLVESGGGLVQPGGSLRLSCAASGFTFS | TYGVH | WVRQSPGKGLEWLG | VIWRGGSTDYSAAFMS | RLTISKDNSKNTVFQMNSLRAEDTAVYFCAK | QAYGHYMDY WGQGTSVTVSS |
| hVH20 | EVQLVESGGGLVQPGGSLRLSCAASGFSFA | TYGVH | WVRQSPGKGLEWLG | VIWRGGSTDYSAAFMS | RLTISKDNSKNTVFQMNSLRAEDTAVYFCAK | QAYGHYMDY WGQGTSVTVSS |
| hVH21 | EVQLVESGGGLVQPGGSLRLSCAASGFSFA | TYGVH | WVRQAPGKGLEWLG | VIWRGGSTDYSAAFMS | RLTISKDNSKNTVFQMNSLRAEDTAVYFCAK | QAYGHYMDY WGQGTSVTVSS |
| hVH22 | EVQLVESGGGLVQPGGSLRLSCAASGFSFA | TYGVH | WVRQSPGKGLEWVS | VIWRGGSTDYSAAFMS | RLTISKDNSKNTVFQMNSLRAEDTAVYFCAK | QAYGHYMDY WGQGTSVTVSS |
| hVH23 | EVQLVESGGGLVQPGGSLRLSCAASGFSFA | TYGVH | WVRQSPGKGLEWLG | VIWRGGSTDYSAAFMS | RFTISRDNSKNTVFQMNSLRAEDTAVYFCAK | QAYGHYMDY WGQGTSVTVSS |
| hVH24 | EVQLVESGGGLVQPGGSLRLSCAASGFSFA | TYGVH | WVRQSPGKGLEWLG | VIWRGGSTDYSAAFMS | RLTISRDNSKNTVFQMNSLRAEDTAVYFCAK | QAYGHYMDY WGQGTSVTVSS |
| hVH25 | EVQLVESGGGLVQPGGSLRLSCAASGFSFA | TYGVH | WVRQSPGKGLEWLG | VIWRGGSTDYSAAFMS | RLTISKDNSKNTLYFQMNSLRAEDTAVYFCAK | QAYGHYMDY WGQGTSVTVSS |
| hVH26 | EVQLVESGGGLVQPGGSLRLSCAASGFSFA | TYGVH | WVRQSPGKGLEWLG | VIWRGGSTDYSAAFMS | RLTISKDNSKNTVLQMNSLRAEDTAVYFCAK | QAYGHYMDY WGQGTSVTVSS |
| hVH27 | EVQLVESGGGLVQPGGSLRLSCAASGFSFA | TYGVH | WVRQSPGKGLEWLG | VIWRGGSTDYSAAFMS | RLTISKDNSKNTVFQMNSLRAEDTAVYYCAK | QAYGHYMDY WGQGTSVTVSS |
| hVH28 | EVQLVESGGGLVQPGGSLRLSCAASGFSFA | TYGVH | WVRQSPGKGLEWLG | VIWRGGSTDYSAAFMS | RLTISKDNSKNTVFQMNSLRAEDTAVYFCAR | QAYGHYMDY WGQGTSVTVSS |
| hVH29 | EVQLVESGGGLVQPGGSLRLSCAASGFSFA | TYGVH | WVRQSPGKGLEWLG | VIWRGGSTDYSAAFMS | RLTISKDNSKNTVFQMNSLRAEDTAVYFCAK | QAYGHYMDY WGQGTSVTVSS |

Figure 3 (Continued)

HUMANIZED ANTI-IL-10 ANTIBODIES FOR THE TREATMENT OF SYSTEMIC LUPUS ERYTHEMATOSUS (SLE)

This application is a Divisional of U.S. Ser. No. 13/512,780, now U.S. Pat. No. 8,852,871, filed May 30, 2012, which is a national stage application of International Patent Application PCT/EP2010/068562, which claims priority to GB 0920933.9, now abandoned, filed Nov. 30, 2009, GB 0920940.4, now abandoned, filed Nov. 30, 2009, and GB 0920942.0 now abandoned, filed Nov. 30, 2009, each of which is hereby incorporated by reference in its entirety.

SEQUENCE DISCLOSURE

This application includes as part of its disclosure a biological sequence listing text file named "43297o1602.txt" which was created on Aug. 29, 2014 and has a size of 60,366 bytes, which is hereby incorporated by reference in its entirety.

FIELD OF THE INVENTION

The present invention is concerned with interleukin-10 (IL-10) and IL-10 specific agents. In particular, the present invention involves humanized IL-10 antibodies and their uses. The invention further envisages a method of treatment of systemic lupus erythematosus (SLE).

BACKGROUND TO THE INVENTION

Systemic lupus erythematosus (SLE) is regarded as an autoimmune disease, in which abnormal hyperactivity of B lymphocytes and massive abnormal production of immunoglobulin gamma (IgG) auto-antibodies plays a key role. This pathological process results in sequestration and destruction of Ig-coated cells, fixation and cleaving of complement proteins, and release of chemotaxins, vasoac-tive peptides and destructive enzymes into tissues (Hahn B H. Systemic Lupus Erythematosus. In: Kasper D L, Braunwald E, Fauci A S, Hauser S L, Longo D L, Jameson, J L, editors. In: Harrison's Principles of Internal Medicine (16th edition). New York (US): McGraw-Hill; 2005. pp. 1960-1967).

SLE is characterized by diverse manifestations. In the course of the disease a total of 95% of patients complain of musculoskeletal disease, 80% show cutaneous lesions, 85% haematological disease, 60% neurological disorders, 60% cardiopulmonary disease, 30% to 50% renal disease, 40% gastrointestinal disease, 15% thrombosis and 15% ocular disease. The vast majority of the patients (95%) also suffer from systemic symptoms such as fatigue, malaise, fever, anorexia, and weight loss, which are present most of the time. Most patients experience disease periods of flares alternating with remissions. Permanent remissions (absence of symptoms with no treatment) are very rare. More than 50 years ago most patients diagnosed with SLE lived less than 5 years. Nowadays, 10 year survival is over 90%, mainly based on earlier diagnosis, symptomatic anti-inflammatory and immune-suppressive treatment. The common cause of death is infection as a result of immune-suppression (Hahn 2005).

Antimalarial, anti-inflammatory and immunosuppressive drugs have routinely been used in the treatment of SLE. Non-steroidal anti-inflammatories have been supplemented with corticosteroids when the symptoms become difficult to control. Further, active SLE, with major organ involvement, requires aggressive therapy with cyclophosphamide.

Up to now, there is no causative treatment available to cure SLE and/or improve patients' quality of life on a long term basis. However, recent advances in antibody technology and the further identification of factors underlying this autoimmune disease have opened up the possibility of using monoclonal antibodies as a treatment option. In particular, a favourable approach to treat SLE would be a specific treatment interacting or correcting the pathological immune response resulting in the massive overproduction of polyclonal auto-antibodies. Since the pathogenesis of SLE primarily involves dysregulated B cells, monoclonal antibodies capable of targeting B-cells are of special interest. As noted by Robak and Robak (Current Drug Targets, 2009, No. 10, pages 26-37) potential B-cell surface antigen targets are CD19, CD20, CD21 and CD22. Further, IL-10, IL-1ra, IL-12 (Capper et al., Clin. Exp. Immunol. 2004 November; 138(2):348-56), and IL-6 (Chun et al., J. Clin. Immunol. 2007 September; 27(5):461-6) are important cytokines in regulating immune response and are especially raised during flares in SLE patients. Plasma levels of IL-10 and auto-antibodies against double-stranded DNA (dsDNA) often mirror disease activity in patients with SLE. Raised IL-10 levels correlated with disease activity in SLE patients (Park et al., Clin. Exp. Rheumatol. 1998 May-June; 16(3):283-8). However, IL-10 is a cytokine with pleiotropic effects on the immune system and is also known to be involved in reducing proinflammatory responses.

Clinical trials with monoclonal antibodies have been conducted in SLE patients. In particular, several trials have involved the antibody Rituximab, a chimeric mouse anti-CD20 monoclonal antibody used for the treatment of non-Hodgkin's lymphoma. As noted by Robak and Robak (2009), the results of these trials show high activity of this antibody in SLE patients, and several new antibodies targeting CD20 have been developed; Ofatumumab, IMMU-106 and GA-101. Further clinical trials reporting activity of monoclonal antibodies in SLE have been completed with the anti-CD22 antibody, Epratuzumab, the anti-TNFα antibody, Infliximab, the anti-IL-10 antibody, B-N10 (Llorente et al., Arthritis Rheum. 2000 August; 43(8): 1790-800), the anti-CD40L antibodies, IDEC 131 and BG 9588, the BLYS inhibitor, Belimumab, the anti-IL6 receptor antibody, Toclimumab, and the anti-C5 antibody Eculizumab.

It is the aim of the present invention to provide further agents, and in particular antibodies, having utility in this area.

Accordingly the present invention provides a humanized or chimeric antibody or fragment thereof capable of binding to interleukin-10 (IL-10), wherein said antibody or fragment thereof is capable of being administered to a subject in the absence of an intolerable increase in the level of proinflammatory cytokines.

Since IL-10 represents an anti-inflammatory cytokine, one would expect upon blocking a dramatic increase of cytokines. For the murine IL-10 antibody, B-N10, where one can observe in unstimulated cell cultures (which reflects the in vivo situations in healthy individuals) an increase in proinflammatory cytokines such as IL-6 or TNF alpha. However, the inventors have surprisingly found that when the antibody of the present invention is applied to the cells in vitro, and administered in vivo, cytokine release is much lower. This lower cytokine release is advantageous as, as a result, the antibody of the present invention is more tolerable to individuals to which it is administered.

The invention will be illustrated by way of example only, with reference to the following Figures, in which:

FIG. 1A shows the amino acid sequence of the light chain variable region of the murine B-N10 antibody (SEQ ID No:2). The hypervariable complementarity-determining regions (CDRs) are underlined (wherein LCDR1 is SEQ ID No: 4; LCDR2 is SEQ ID No: 5; and LCDR3 is SEQ ID No:6).

FIG. 1B shows the amino acid sequence of the heavy chain variable region of the murine B-N10 antibody (SEQ ID No: 3). The hypervariable complementarity-determining regions (CDRs) are underlined (wherein HCDR1 is SEQ ID No: 7; HCDR2 is SEQ ID No: 8; and HCDR3 is SEQ ID No:9).

FIG. 2A shows the nucleotide sequence encoding the light chain variable region of the murine B-N10 antibody (SEQ ID No: 10).

FIG. 2B shows the nucleotide sequence encoding the heavy chain variable region of the murine B-N10 antibody (SEQ ID No: 11).

FIG. 3 shows the amino acid sequence of the murine B-N10 light and heavy chain variable regions (SEQ ID Nos: 12 and 13, respectively) together with the sequences taken from A17 (SEQ ID No: 14), JK1 (SEQ ID No: 15), 3-66+04 (SEQ ID No: 16) and JH4 (SEQ ID No: 17) and the variable regions hVL1 to hVL12 (SEQ ID Nos: 18 to 29) and the variable regions hVH1 to hVH29 (SEQ ID Nos: 30 to 58) generated during the humanization of the murine B-N10 antibody.

Figure 4:
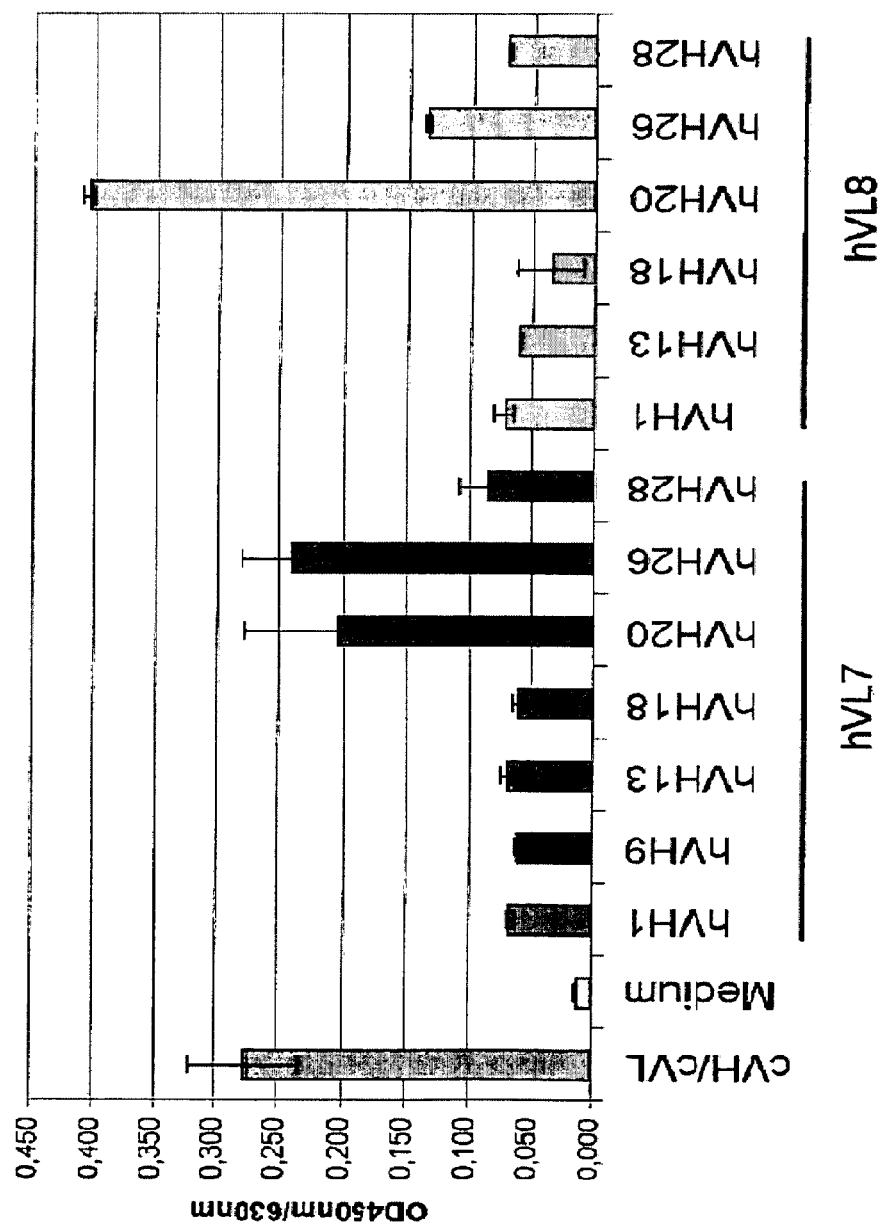

FIG. 4 provides a comparison of the antigen binding properties of the humanized antibody variants in comparison to a chimeric cB-N10 antibody using the hIL-10 antigen ELISA.

Figure 5:
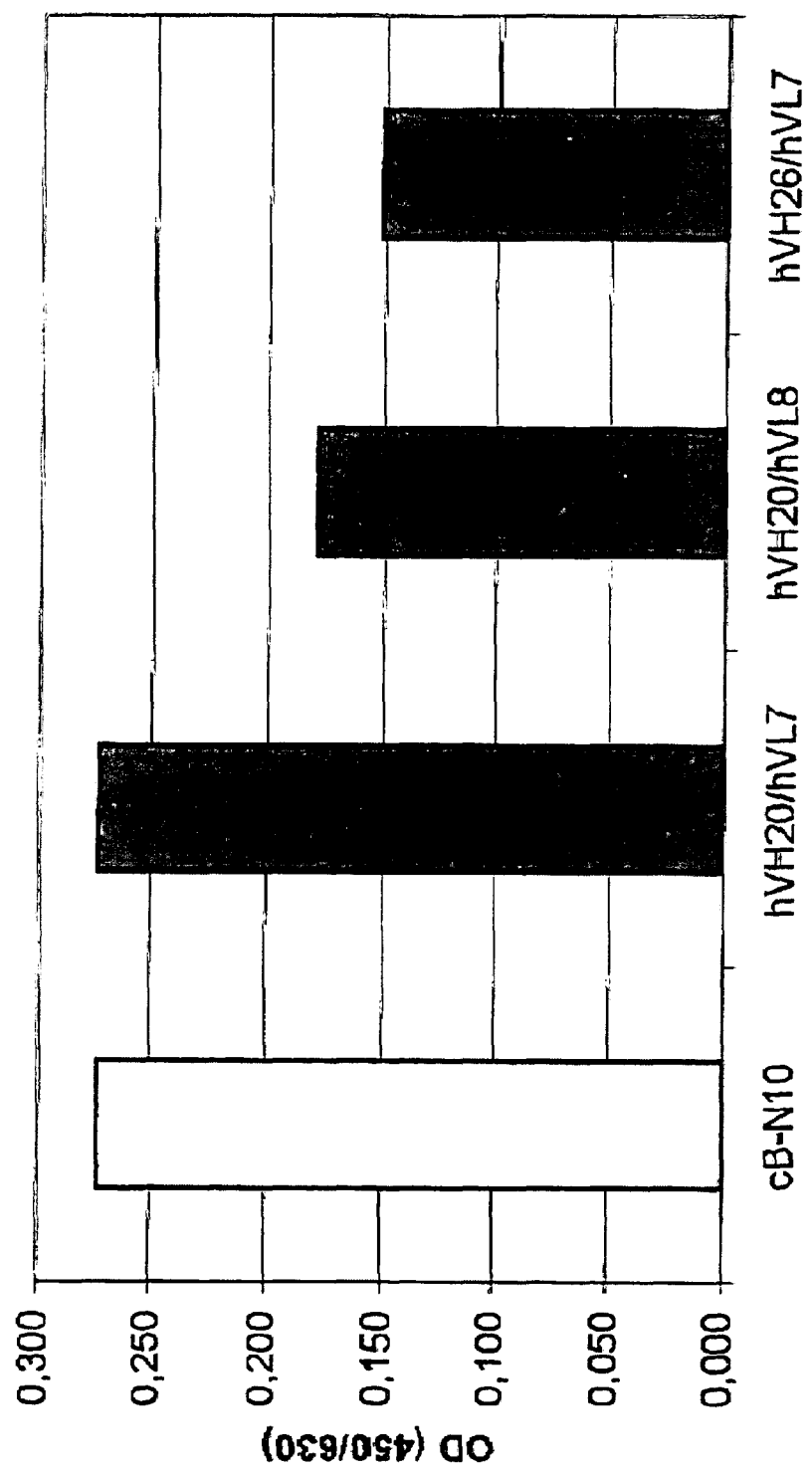

FIG. 5 provides the result of the determination of the binding properties of the three humanized variants, hVH20/hVL7, hVH20/hVL8 and hVH26/hVL7, in comparison to the chimeric B-N10 antibody using purified antibody preparations.

Figure 6A:
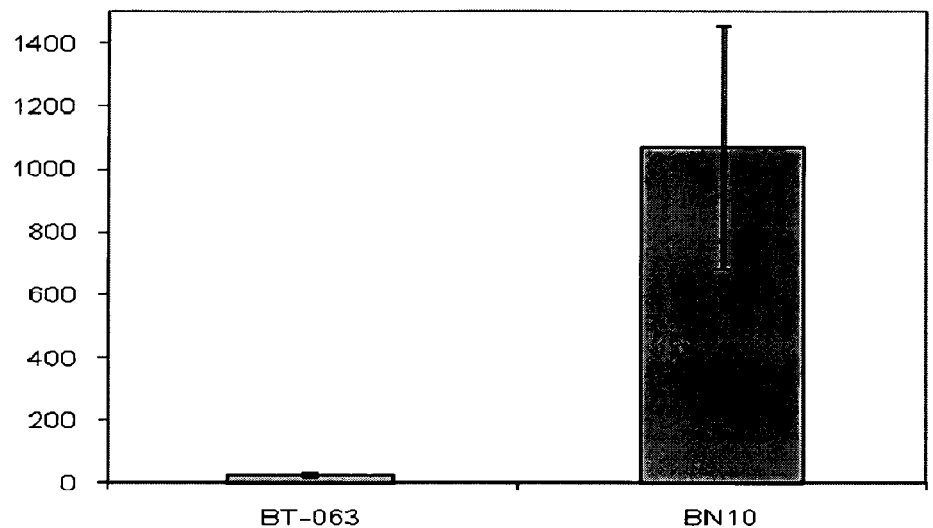

FIG. 6A shows the level of TNFalpha release from whole blood cultures from healthy volunteers after incubation with B-N10 compared to BT-063 (at 50 μg/ml).

Figure 6B:
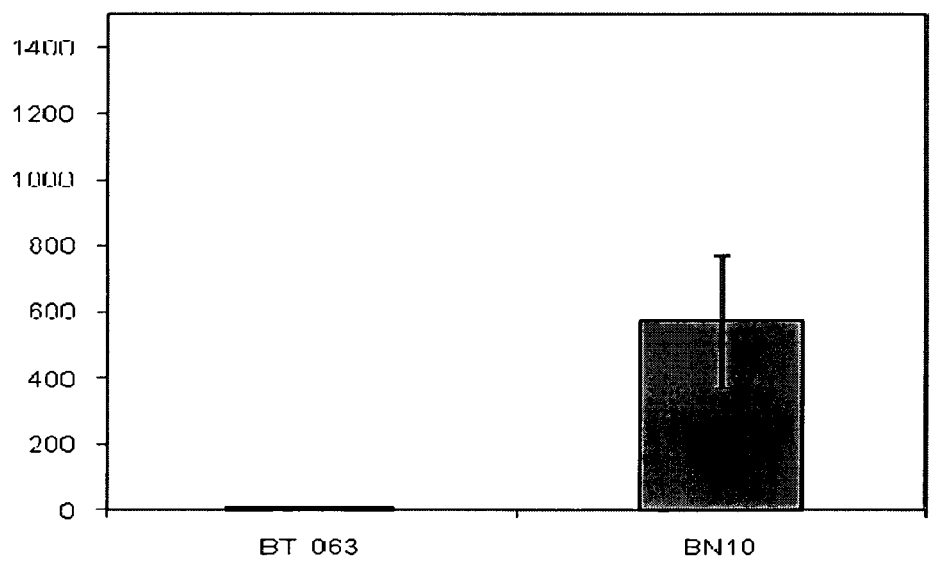

FIG. 6B shows the level of TNFalpha release from whole blood cultures from SLE patients after incubation with B-N10 compared to BT-063 (at 50 μg/ml).

Figure 7A:
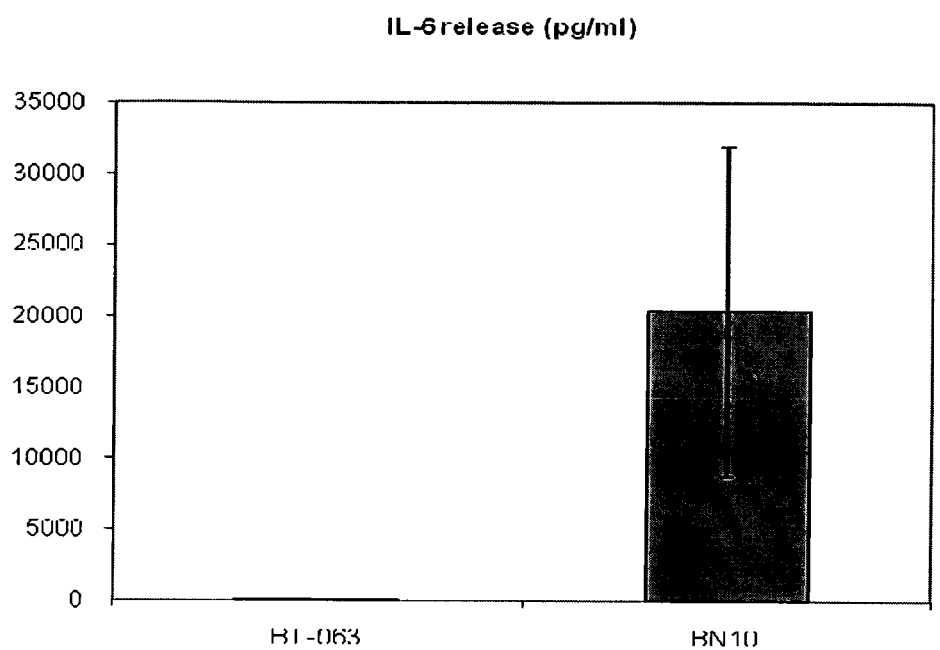

FIG. 7A shows the level of IL-6 release from whole blood cultures from healthy volunteers after incubation with B-N10 compared to BT-063 (at 50 μg/ml).

Figure 7B:
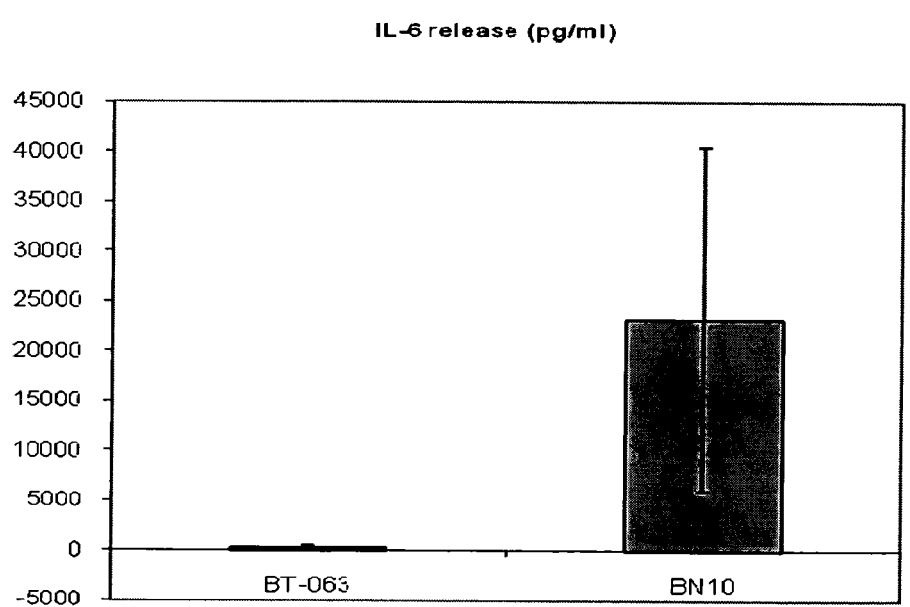

FIG. 7B shows the level of IL-6 release from whole blood cultures from SLE patients after incubation with B-N10 compared to BT-063 (at 50 μg/ml).

Figure 8A:
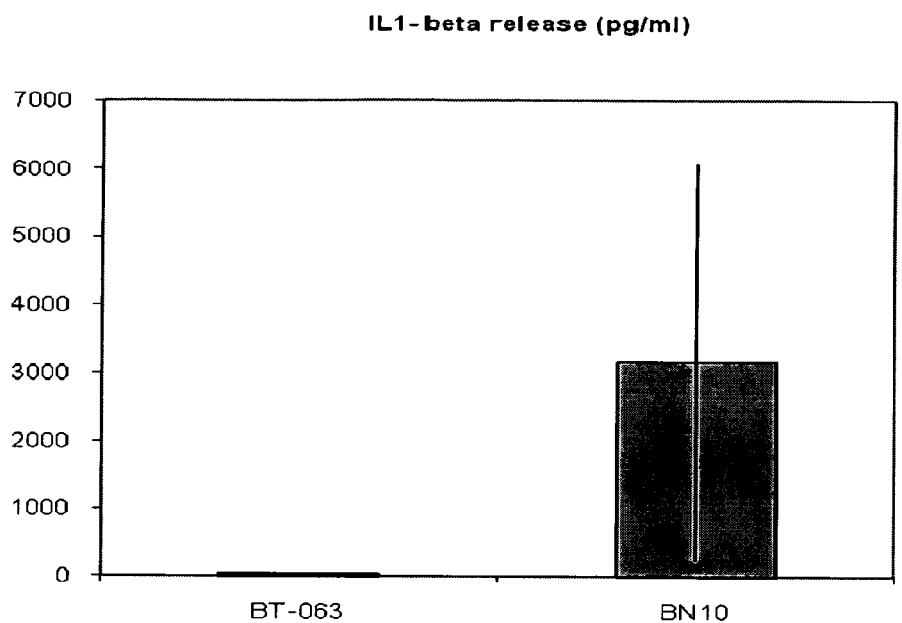

FIG. 8A shows the level of IL-1beta release from whole blood cultures from healthy volunteers after incubation with B-N10 compared to BT-063 (at 50 μg/ml).

Figure 8B:
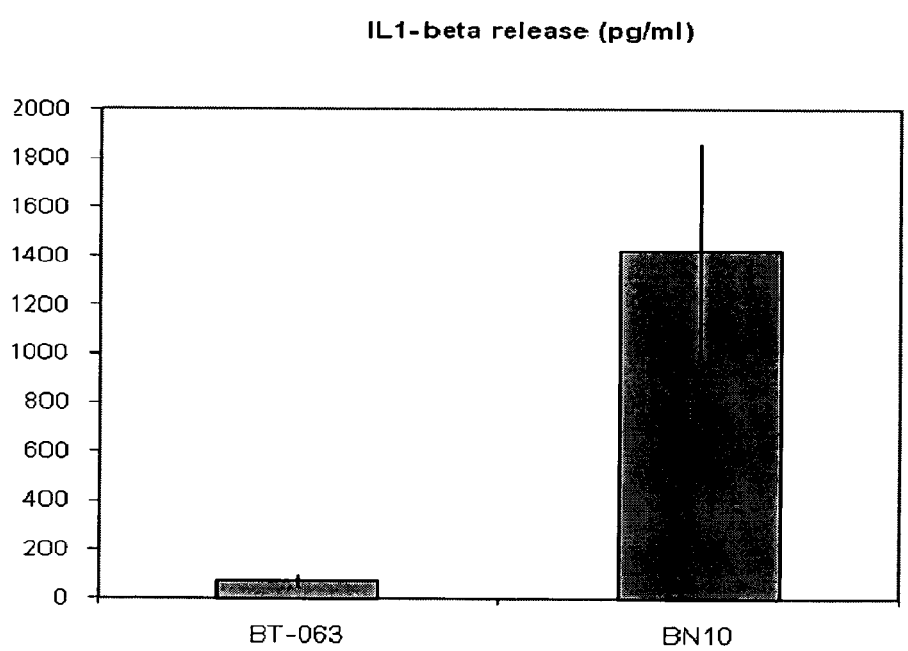

FIG. 8B shows the level of IL-1 beta release from whole blood cultures from SLE patients after incubation with B-N10 compared to BT-063 (at 50 μg/ml).

Figure 9A:
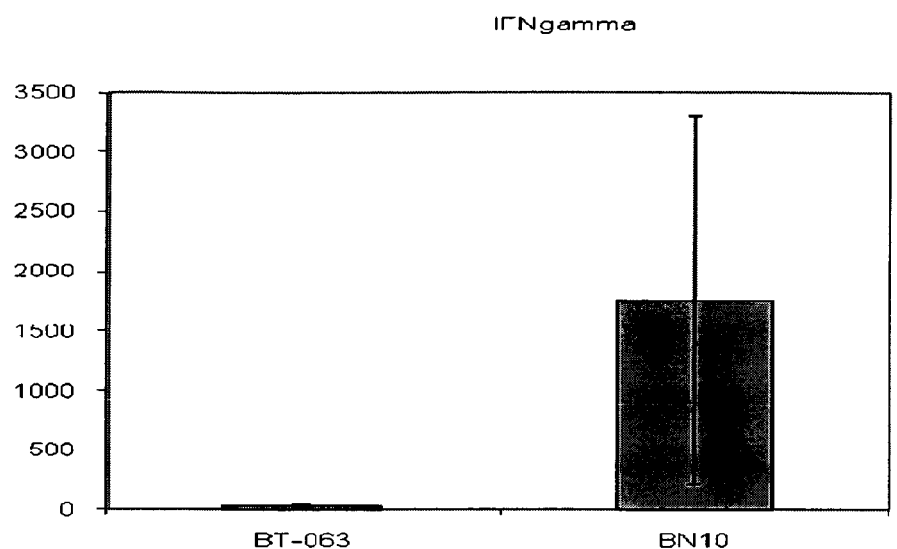

FIG. 9A shows the level of IFN gamma release from whole blood cultures from healthy volunteers after incubation with B-N10 compared to BT-063 (at 50 μg/ml).

Figure 9B:
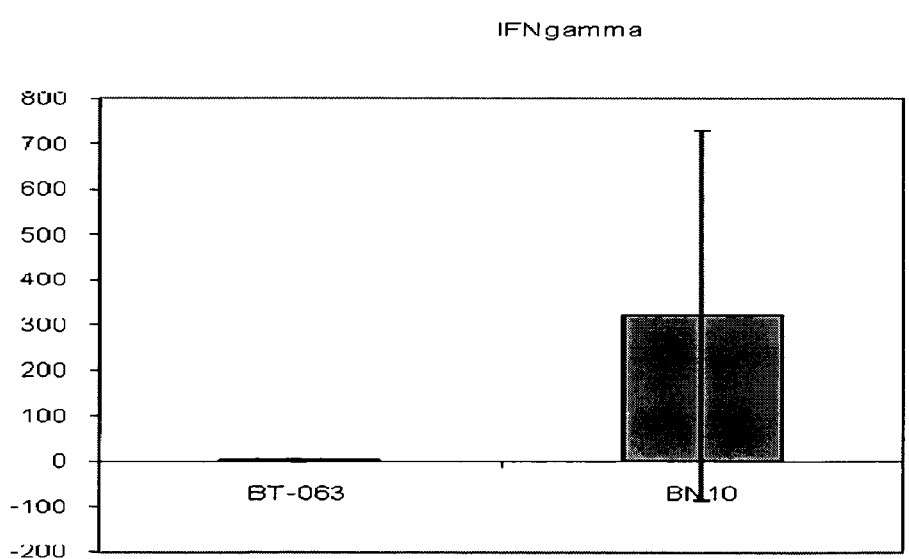

FIG. 9B shows the level of IFN gamma release from whole blood cultures from SLE patients after incubation with B-N10 compared to BT-063 (at 50 μg/ml).

Figure 10:
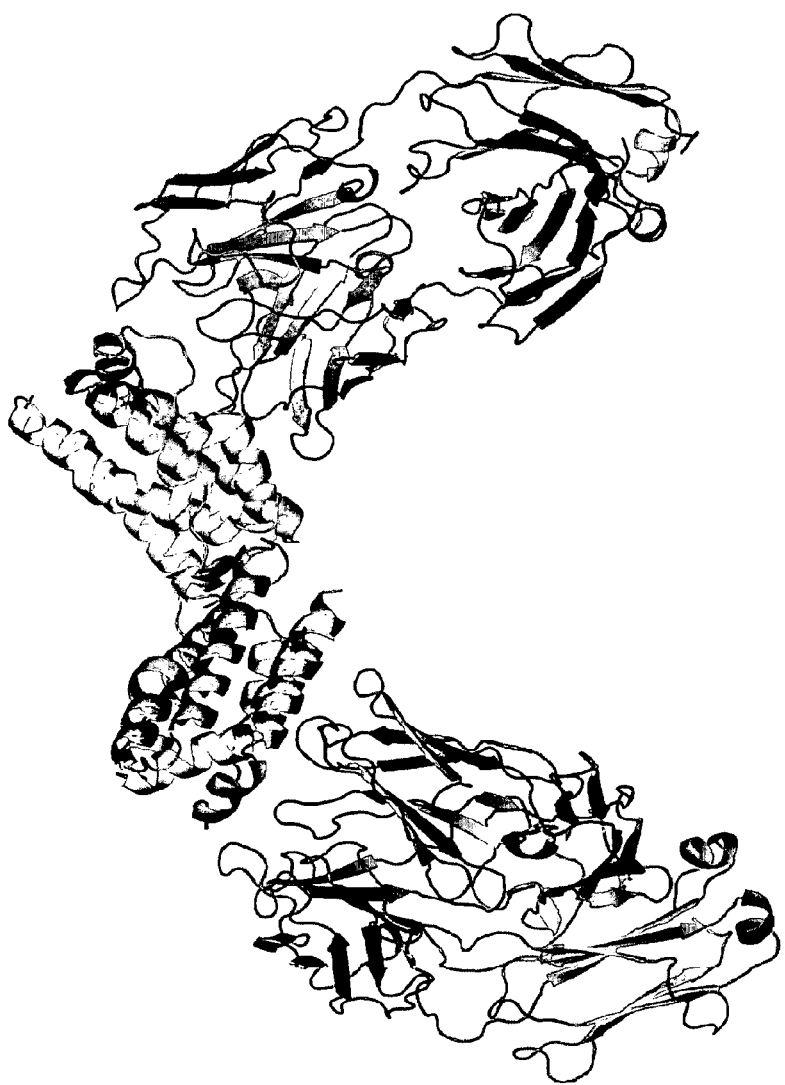

FIG. 10 shows the overall structure of the Fab fragment of BT-063 binding IL-10. IL-10 and the Fab fragment are shown as a ribbon representation.

Figure 11:

FIG. 11 shows the Fab fragment of BT-063 addresses the same binding site on IL-10 as the IL-10 receptor. IL-10, IL-10R1 and the Fab fragment are shown as a ribbon representation.

Figure 12:
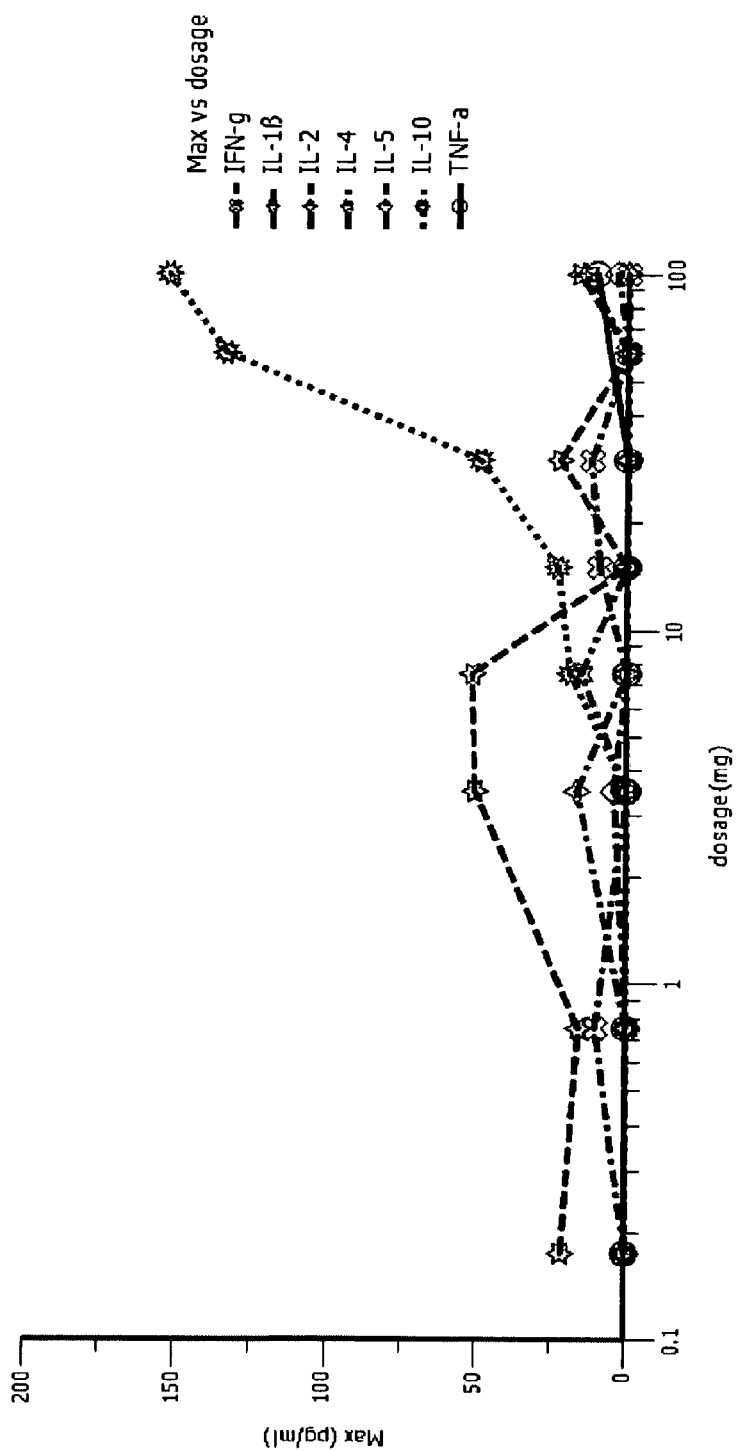

FIG. 12 shows a graph of mean cmax of cytokine concentration in plasma versus dosage after administration of BT-063 to healthy volunteers.

Figure 13:
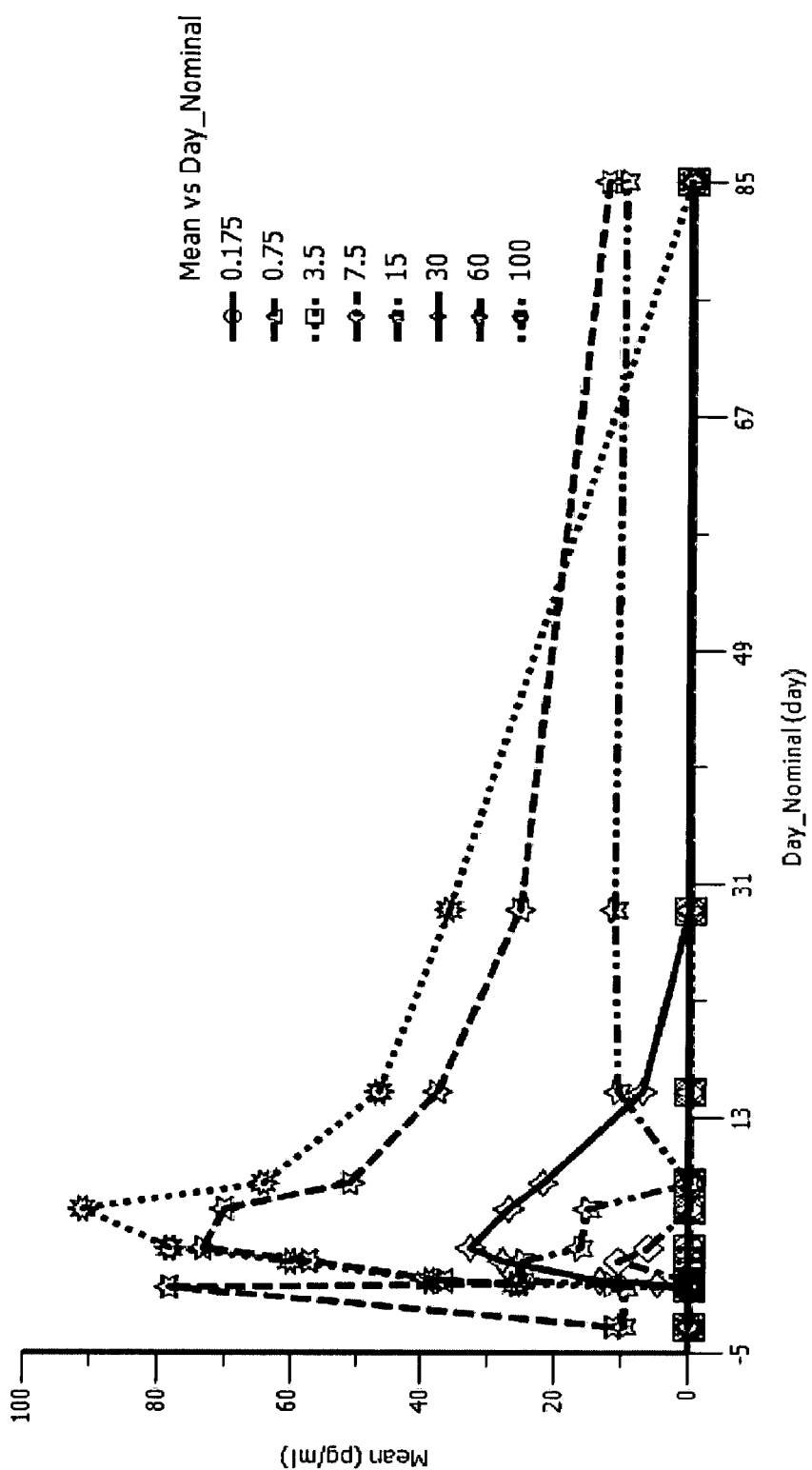

FIG. 13 shows a graph of mean IL-10 concentration in plasma over time after in vivo administration of BT-063 in healthy volunteers.

DETAILED DESCRIPTION OF THE INVENTION

The present invention relates to a humanized or chimeric antibody or fragment thereof capable of binding to interleukin-10 (IL-10), and the use of this antibody or fragment thereof in the treatment of medical conditions that are mediated by an elevated level or activity of IL-10.

Human IL-10 is a homodimer with a molecular mass of 37 kDa. Each monomer consists of 160 amino acids and has a molecular mass of 18.5 kDa. The TL-10 dimer interacts with the IL-10R receptor alpha (IL-Rα or IL-10R1) and subsequently recruits IL-10 receptor beta (IL-10Rβ or IL-10R2) into the complex. The receptor is expressed on a variety of cells, in particular immune cells (Asadullah et al., Pharmacol. Rev. 2003 June; 55(2):241-69) including most hematopoietic cells such as monocytes, macrophages, and T- and B-lymphocytes, but is also expressed on non-hemopoietic cells, such as epidermal cells or keratiocytes. The binding of IL-10 receptor alpha by IL-10 and the recruitment of IL-10 receptor beta leads to signal transduction via Jak1 and Tyk2 tyrosine kinases and subsequently to activation of transcription factors of the STAT family. Various cellular sources of IL-10 are known, such as T helper cells, regulatory T cells, monocytes, macrophages, B cells, eosinophils, mast cells, keratinocytes, dendritic cells and even cancer cells. IL-10 functions on B cells range from prevention of apoptosis, enhancement of proliferation, class switching events and differentiation into plasma cells (Asadullah et al., Pharmacol. Rev. 2003 June; 55(2):241-69).

The present invention provides a humanized or chimeric antibody or fragment thereof capable of binding to interleukin-10 (IL-10), wherein said antibody or fragment thereof is capable of being administered to a subject in the absence of an intolerable increase in the level of pro-inflammatory cytokines.

In particular, it is known that the administration of therapeutic antibodies can lead to an intolerable increase in the levels of pro-inflammatory cytokines which lead to adverse side effects in the subject. In particular, the intolerable increase can cause the reddening of the skin and induce a fever or flu-like symptoms, including an increase in body temperature. Accordingly, in a preferred aspect of the invention the antibody or antibody fragment is one which is capable of being administered to a subject in the absence of an increase in body temperature of greater than 2° C.

Further, the antibody or fragment thereof does not cause a substantial increase in the amount of pro-inflammatory cytokines in the subject's blood plasma after administration. Levels of these cytokines which are intolerable are usually several times greater than the cytokines upper limit of normal (ULN). where the ULN is defined as the mean level of a cytokine(s) measured in a subject cohort plus 2× standard deviations.

Accordingly, in a preferred aspect of the invention the antibody or fragment thereof is capable of being administered to a subject in the absence of an increase of the pro-inflammatory cytokine which is greater than 500%, more preferably greater than 300%, of the upper limit of normal (ULN). In other words, the antibody or fragment thereof causes an increase in the level of a pro-inflammatory cytokine which is less than 500%, more preferably less than 300% of the ULN for that cytokine. It is preferred that the pro-inflammatory cytokine is at least one, and preferably all, of TNF-α, IFN-γ, and IL-1 beta. Alternatively, the pro-inflammatory cytokine and is not IL-6 or IL-8.

Still further, it is particularly preferred that the antibody or fragment thereof of the present invention is capable of inducing IL-1 receptor antagonist (IL-1ra) in the subject, which leads to an anti-inflammatory response.

In a preferred aspect of the present invention the humanized antibody or fragment thereof does not elicit a greater than 500% increase in the level of a pro-inflammatory cytokines, especially TNFalpha, IL-1beta, IL-6 released from a PBMC, more particularly an immune cell, when contacted with said cell in vitro.

The present inventors have surprisingly found that the humanized antibody or fragment thereof of the invention elicits a smaller increase in the level of pro-inflammatory cytokines in in vitro assays than the murine B-N10 antibody.

The level of pro-inflammatory cytokine release can be determined by in vitro studies utilizing human whole blood cultures, such as those studies described below in Example 5, or isolated immune cells. In particular, the methods comprise the steps of: (a) incubating a cell culture with the antibody or fragment thereof; (b) and determining the level of at least one pro-inflammatory cytokine.

The human whole blood cultures can be taken from healthy or diseased patients, such as those suffering from SLE. The peripheral blood mononuclear cell (PBMC) can be an immune cell, and, in particular, selected from macrophages, monocytes, dendritic cells, T helper cells and B cells.

The at least one proinflammatory cytokine can be selected from, interleukin-1 beta (IL-1beta), IL-1 alpha, IL-6, or tumor necrosis factor alpha (TNF-alpha) or T helper cytokines (interferon gamma, IFN-gamma, IL-4), macrophage cytokine (IL-12), chemokines (IL-8, MCP-1) respectively. The levels of such cytokines which are released can be measured in the cell culture supernatant using methods which are generally known in the art.

More particularly this in vitro method can comprise the steps of:
a) contacting 50 μg/ml of the antibody or fragment with a human whole blood culture;
b) incubating said antibody or fragment with said whole blood culture at 37° C. for 48 hours;
c) determining the quantity of one or more pro-inflammatory cytokines in the culture.

In particular, the method is run simultaneously with human whole blood culture which has not been contacted with the antibody Preferably, when compared to this control the antibody or antibody fragment of the present invention causes a less than 500% increase in the level of the cytokine, more preferably a less than 300% increase in the level of the cytokine. It is preferred that the cytokine in this method is not IL-6 or IL-8.

Cytokines can be detected in the culture with a Multiplex Bead Immunoassays (solid-phase protein assays which are carried out in 96-well filter plates). The method relies on the use of beads which are linked, firstly, with a specific antibody against a specific cytokine and, secondly, exhibit defined spectral characteristics. This enables the beads to be identified specifically and thus to assign them to the known, linked antibody. The cytokine bound to the bead can be quantified by means of further binding of the cytokines by a detection antibody. This makes it possible to detect simultaneously up to 10 human cytokines, including GM-CSF, IL-1β, IL-2, IL-4, IL-5, IL-6, IL-8, IL-10, IFN-γ and TNF-α. Filter plates are used for this purpose into whose moistened wells the samples, standards and the bead solution are pipetted. After incubation, the liquid is aspirated off with a vacuum pump, the beads left behind are washed, and a mixture of biotinylated detection antibodies is added. Unbound detection antibodies are removed by aspirating off the liquid and washing the beads remaining in the well, and then streptavidin-conjugated R-phycoerythrin (streptavidin-RPE) is added. This recognises the biotinylated detection antibodies during incubation, and after washing again, the immune complexes formed can be analysed by the Bio-Plex 200 System. The immunoassay is analysed using the Bio-Plex 200 device. This uses two laser systems, which, firstly, identify the beads on the basis of their spectral characteristics and, secondly, determine the quantity of bound cytokines by detection using a secondary antibody. The quantification of the bound quantity is achieved by means of standards run in parallel with known quantities of cytokines.

The present invention also provides a humanized or chimeric antibody or fragment thereof capable of binding to interleukin-10 (IL-10), wherein said antibody or fragment thereof is capable of increasing plasma levels of IL-10 when administered to a subject.

As demonstrated in Example 8 below, while the antibody of the present invention can be administered in the absence of an intolerable increase in the level of pro-inflammatory cytokines, administration increases the amount of IL-10 detectable in plasma samples in a dose dependent fashion. This finding, that IL-10 levels would increase when a neutralizing antibody is applied, is unexpected. It would be usual to expect that the administration of a cytokine neutralizer would reduce the level of free cytokine (Strand et al., Nature Reviews Drug Discovery, 2007, Vol. 6, pages 75-92). While not wishing to be bound by theory it is thought that binding of IL-10 by the antibody prevents IL-10 binding to the IL-10 receptor and triggers a negative feedback loop which causes B-cells to produce more IL-10. Nevertheless, the upregulation does not prevent the therapeutic utility of the antibody of the present invention since, also as demonstrated in Example 8, the antibody is safe to administer at levels high enough to neutralize all IL-10.

Within the present application the term "chimeric antibody" refers to antibodies in which a portion of the heavy and/or light chain is identical with sequences in antibodies derived from a particular species or belonging to a particular antibody class or subclass, while the remainder of the antibody is identical with sequences in antibodies derived from a different species, antibody class or subclass. It is particularly preferred that the CDRs of a chimeric antibody have one origin, while the remainder of the antibody has a different origin. In particular, in the present invention the chimeric antibody may be a humanized antibody in which the antigen binding sequences/variable domains of a non-human antibody have been grafted onto human antibody framework regions.

Within the present application the term "fragment" refers to a fragment or a derivative of an antibody that still retains the desired biological activity. The fragment will generally comprise the antigen binding region of the antibody and, in particular, the Fab, Fab', F(ab)'$_2$, Fv and scFv fragments, as well as multivalent antibody derivatives, in particular diabodies or tandem diabodies. The fragment is at least 25, more preferably 50 and still more preferably 200 to 500 amino acids. Alternatively the fragments can be defined as those having of size of between 30 KDa and 150 kDa.

Further, the antibody fragments may involve two or more peptide/polypeptide chains. For example an Fab fragment comprising two chains of between 200 and 300 amino acids in length each or TandAbs® (tetravalent bispecific antibody formats) comprising two chains of between 400 and 500 amino acids in length each.

It is a preferred feature of the invention that the antibody or fragment thereof is derived from the murine B-N10 antibody or the humanized BT-063 (variant hVH26/hVL7) antibody described herein. In particular, such an antibody or fragment thereof will comprise CDRs being at least 80% identical to those of CDR 1, CDR 2 and CDR3 of B-N10/BT-063 variable light chain and/or comprises amino acid sequences at least 80% identical to those of CDR 1, CDR 2 and CDR3 of B-N10/BT-063 variable heavy chain. The amino acid sequence of the murine CDRs is shown in FIG. 1. The amino acid sequence of the BT-063 CDRs is shown in Example 6. More preferably the sequences will be at least 90%, or at least 95% identical to those of the CDRs of the B-N10/BT-063 antibody. The X ray crystallography studies described in Example 6 herein indicate which residues within the CDRs are important for binding to IL-10.

Alternatively, the antibody or fragment of the invention, while still being derived from the B-N10/BT-063 antibody, can comprise an amino acid sequence of CDR 1, CDR 2 and CDR3 of the B-N10/BT-063 variable light chain and/or an amino acid sequence of CDR 1, CDR 2 and CDR3 of B-N10/BT-063 variable heavy chain, optionally with variation in these sequences which does not substantially alter the affinity and/or specificity of the antibody or fragment thereof. In particular, the variations in the sequence do not reduce the affinity or specificity of the antibody or fragment for IL-10 as compared to that of an antibody or fragment comprising the CDRs of the murine B-N10 antibody or the BT-063 (variant hVH26/hVL7) antibody.

In a specific embodiment the present invention provides a humanized or chimeric antibody or fragment thereof which comprises the amino acid sequences of CDR 1, CDR 2 and CDR3 of the B-N10/BT-063 variable light and/or heavy chains. More preferably the present invention provides a humanized or chimeric antibody or fragment thereof which comprises the amino acid sequences of the variable domains of the murine antibody B-N10, as shown in FIG. 1. Most preferably the antibody or fragment comprises one or both of the amino acid sequences of the variable domains of BT-063 (SEQ ID No: 69 and SEQ ID No: 70).

Generally, the antibody of the invention further comprises a human constant region (Fc). This can be selected among constant domains from any class of immunoglobulines, including IgM, IgG, IgD, IgA and IgE, and any isotype, including IgG1, IgG2, IgG3 and IgG4. Preferred constant regions are selected among constant domains of IgG, in particular, IgG1.

Other Products

The present invention further provides nucleic acid sequences encoding the antibody or antibody fragments described above. The nucleic acid sequences may be DNA or RNA but are preferably DNA. The sequences may be used within expression cassettes or vectors, and are of particular use in producing the antibodies and fragments thereof disclosed herein.

The invention further provides host cells transformed with these polynucleotides, expression cassettes or vectors. Suitable host cells can be both prokaryotic and eukaryotic.

Alternatively, the host cell can be a hybridoma obtained by fusing a cell producing an antibody of the present invention with a myeloma cell.

The host cells described above can be utilized in a method for the production of an antibody or fragment thereof. In particular, such a method may comprise a step of culturing the host cell in a suitable culture medium under conditions allowing the expression of the antibody or fragment thereof and separating the antibody or fragment from the culture medium. Methods of this type are well known and described in the art.

Medical Uses

The antibodies and fragments thereof described herein have utility in the treatment of diseases or medical conditions which are mediated by an elevated level or activity of IL-10. As a result, provided is a method for treating or preventing a medical condition in a subject, wherein the medical condition is mediated by an elevated level or activity of IL-10, comprising administering a therapeutically effective amount of the antibody or fragment thereof described herein.

In particular, the medical condition which is mediated by an elevated level or activity of IL-10 is SLE. Accordingly, the present invention also provides an antibody or fragment thereof as described herein for use in the treatment of SLE.

Further examples are thrombocytopenic purpura, lupus nephritis, HIV, hCMV and hepatitis C. The treatment of tumor cells depending on IL-10 by direct support of proliferation or suppression of immune response is another example.

A further embodiment of the invention is a pharmaceutical composition comprising the antibody or fragment thereof described above with a pharmaceutically acceptable carrier or diluent. In one embodiment the composition comprises liposomes to which the antibody or fragment thereof is coupled.

Such compositions can be administered to the patient parenterally, intravenously or subcutaneously. Preferably in the treatment of SLE the antibody or fragment thereof is administered intravenously or subcutaneously.

The antibodies and fragments thereof are of particular use in the treatment of disease, since, as they do not cause a significant increase in the levels of pro-inflammatory cytokines, they do not require the co-administration of a corticosteroid to prevent a "cytokine storm" which would be intolerable to the patient.

Thus, in a particular aspect the present invention provides a method for treating or preventing a medical condition in a subject, wherein the medical condition is mediated by an elevated level or activity of IL-10, comprising administering a therapeutically effective amount of an antibody or fragment thereof as described herein to said subject, wherein the subject is not simultaneously or separately treated with a corticosteroid, i.e. the patient is one who is not concurrently being treated with a corticosteroid. In an embodiment of this preferred aspect the medical condition mediated by an elevated level or activity of IL-10 is SLE.

Corticosteroids are currently used to treat SLE in many patients. However, this aspect of the invention has particular utility in the treatment of patients where the administration of corticosteroids is no longer desirable.

Non-Medical Uses

Still further provided is a labeled humanized or chimeric antibody or fragment thereof comprising the antibody or fragment thereof described herein and a label. The label may be of any suitable type known in the art for detecting the presence of an antibody in a sample. In particular, the label may be a fluorescent label.

The labeled or unlabeled antibody, and in particular the labeled antibody, has specific utility in an in vitro method for detecting the presence of IL-10 in a sample. The method may comprise a step of contacting the unlabeled or labeled antibody or fragment thereof with the sample, washing the sample to remove antibody and fragments thereof which are not bound to the sample (i.e. unbound antibody or antibody fragments) and detecting the presence of the antibody (or fragment), for example via the label, in the sample.

Alternatively, the unlabeled antibody or fragment may be used for an in vitro method for neutralizing IL-10 in a sample. Such a method comprises the steps of contacting the sample with the antibody or fragment thereof so as to bind the antibody or fragment thereof to the IL-10.

The invention will now be described further in relation to the following specific embodiments.

EXAMPLES

Example 1

Characterisation of Murine Anti-IL10 Antibody B-N10

1.1. Isolation of DNA Encoding the Variable Antibody Domains of B-N10

For the identification of the variable sequences of murine BN-10 cell pellets were used. The samples (3×B-N10, Passage 3, 1×10$^7$ cells) were stored at −80° C. until mRNA was isolated from the cells and, after cDNA synthesis, the variable sequences of B-N10 were amplified by PCR and then cloned.

In total 14 clones were sequenced (SEQ Laboratories, Gottingen) and analysed for both the variable light chain and for the variable heavy chain. The variable sequences of the B-N10 were determined unequivocally. Deviations occurred only in the N-terminal primer regions (see Table 1). In the case of the variable heavy chain, the sequence variant QVQLKQ (SEQ ID No: 59) occurred nine times in the primer region, but other variations occurred only once or twice. This variant was chosen for subcloning. In the case of the variable light chain, two variants were present in equal proportions. After comparing the sequences with the murine germ line sequences, the cr1 sequence with only 3 mutations exhibited great homology with the identified VL sequence. This means that the DVLMTQ (SEQ ID No: 60) sequence is most probably the correct sequence. The sequence DIVMTQ (SEQ ID No: 61) is typical of another class of germ line sequence and was therefore excluded.

TABLE 1

Occurrence of N-terminal sequence variants of the sequenced variable light and heavy chain of B-N10. The chosen sequences are indicated in bold type.

| | Sequence | Number |
|---|---|---|
| Variable light chain | DIVMTQ (SEQ ID No: 61) | 5 |
| | DVLMTQ (SEQ ID No: 60) | 5 |
| | DVLMTR (SEQ ID No: 62) | 1 |
| | DIVITQ (SEQ ID No: 63) | 1 |
| | DIVLTQ (SEQ ID No: 64) | 2 |
| Variable heavy chain | QVQLKQ (SEQ ID No: 59) | 9 |
| | QVQLKE (SEQ ID No: 65) | 2 |
| | EVQLQQ (SEQ ID No: 66) | 1 |
| | QVQLNQ (SEQ ID No: 67) | 1 |
| | QVQLTQ (SEQ ID No: 68) | 1 |

The protein sequences of the variable light chain VL and variable heavy chain VH are shown in FIGS. 1A and 1B, respectively. The hypervariable complementarity-determining regions (CDRs) are underlined. The corresponding DNA sequences are shown in FIGS. 2A and 2B, respectively.

Example 2

Generation of a Chimeric B-N10 Antibody

The identified variable sequences of the heavy and light antibody chain from Example 1 were cloned into a vector system for the expression of recombinant antibodies. The first step was to clone the sequences into a BS leader; the N terminal adds a secretion signal and the C terminal adds a splice-donor sequence. The second step was to clone these sequences into the expression vectors which contain the constant human kappa chain and the constant human gamma-1 chain respectively. The vector for the light chain and the vector for the heavy chain were prepared and then transiently co-transfected into COS-7 cells by calcium phosphate precipitation or by lipofection. The cell culture supernatant was harvested after 2 days. After expression of the chimeric B-N10 in COS-7 cells and detection of an antibody titre in the supernatant (sandwich ELISA), its specific binding capacity to human interleukin 10 (R&D Systems, Cat. No. 217-IL/CF, Lot ET114021, stored at −20° C.) was tested in the ELISA.

For the sandwich ELISA a mouse anti-human kappa chain antibody (Becton Dickinson) was bound to the plate surface as a catcher antibody, then incubated with cell culture supernatant and the presence of the chimeric antibody was detected with a POD-conjugated rabbit anti-human IgG (H+L) antibody (Dianova). A chimeric control antibody in defined concentrations (0.125 to 12 µg/mL) was used as a positive control.

For the antigen ELISA, human IL-10 was bound to the plate surface in a concentration of 0.5 and 5 µg per mL. After incubation with the cell culture supernatant (undiluted and diluted 1:5), the binding of the chimeric B-N10 was detected with the POD-conjugated rabbit anti-human IgG (H+L) antibody (Dianova). The murine B-N10 was used as a positive control. The antibody was used in a concentration of 0.5 and 5 µg per mL and binding was detected with a POD-conjugated rabbit anti-mouse IgG/IgM antibody (Dako).

The results of the ELISA are discussed in Example 3.

Example 3

Humanization of Anti-IL10 Antibodies

Initial efforts to reduce the immunogenicity of rodent antibodies in humans involved the generation of chimeric antibodies by replacing rodent by human constant antibody domains. As the rodent framework regions within the variable domains might still induce an immune response the more advanced method of CDR grafting was developed, meaning the transfer of the antigen binding sequences (complementarity determining regions, CDR) onto completely human antibody frameworks (humanization). Usually human acceptor frameworks are selected that resemble most closely the murine donor antibody to increase the probability of restoring the original antigen specificity and affinity during the humanization process. Different approaches using human antibody germline sequences, consensus sequences of expressed antibodies, analysis of CDR loop structures and X-ray structures of antibody/antigen complexes might be used or combined to improve the process. Usually several humanized antibody variants are generated in this way and analysed afterwards regarding their biological effects which might differ from each other and the original antibody. Finally according to the desired function of the antibody a suitable human constant region might be selected.

3.1 Sequence Comparisons Between the Murine Variable Sequences of B-N10 and Human Sequences, and Design of a Set of Humanized VL (hVL) and VH (hVH) Sequences The murine anti-IL-10 antibody B-N10 was selected (Llorente et al., Eur. Cytokine Netw. 1993 November-December; 4(6): 421-7; and Llorente et al., Arthritis Rheum. 2000 August; 43(8): 1790-80). The method for obtaining humanized antibodies is based on the CDR-grafting procedure where the complementary determining regions (CDRs) are fused to human acceptor regions.

The choice of human acceptor frameworks was based on a combined analysis of three data sets:
1. The homology of the murine sequences to human germline sequences to minimize risk of somatic mutations:
2. The comparison of the murine sequences to human consensus sequences to identify unusual amino acid residues and
3. The identification of the canonical structure classes of the CDR sequences to obtain information about important structural framework amino acid residues.

The murine variable light chain of the B-N10 shows the highest homology to the human germline variable segment 2-30*01 (A17 (SEQ ID No: 14)) and to the joining segment JK1 (SEQ ID No: 15). The human consensus sequence with highest homology to B-N10 is HuKII. Complementarity determining regions (CDRs) of the variable light chain could be classified in case of L1 to class 4, and in cases of L2 and L3 to class 1. Critical amino acid residues were identified.

Sequence comparison between mouse CDR and human germline VL genes with the canonical structure of class 4-1-1 revealed highest homology with 2-30*01 (the lowest number of mismatching amino acids).

The murine variable heavy chain of the B-N10 shows the highest homology to the human germline variable segment VH3-33 and to the joining segment JH4 (SEQ ID NO: 17). The human consensus sequence with highest homology to B-N10 is HuHIII. Complementarity determining regions (CDRs) of the variable heavy chain could be classified in case of H1 and H2 to class 1. Critical amino acid residues were identified. Sequence comparison between mouse CDR and human germline VH genes with the canonical structure of class 1-1 revealed highest homology with 3-66*04 (SEQ ID No: 16) (the lowest number of mismatching amino acids). Therefore, the germline sequence VH3-66 was taken too in consideration.

All data obtained were considered to design a set of different variable sequences of humanized variable light (12 variants) and variable heavy chains (29 variants).

3.2 Construction of a Small Library and Selection of Humanized hIL-10 Binding Antibody Fragments In order to generate a library of potentially hIL-10 binding antibody fragments to achieve the optimal human IL-10 binding antibody, the cDNA sequences coding for the 12 hVL and the 29 hVH fragments, as shown in FIG. 3, were generated under consideration of the codon usage of eucaryotic cells.

The obtained cDNAs were cloned subsequently into cloning vectors and sequenced at SEQ Laboratories (Gottingen, Germany). The library was constructed in a way, that each of the 12 cDNAs coding for the hVL fragments were combined with the 29 cDNAs coding for the hVH fragments resulting in 348 potentially expressed antibody fragments.

Following the bacterial expression and two rounds of selection on human IL-10 (R&D Systems, Cat.-No 217-IL/CF) the antibody fragments were analysed by ELISA for binding to hIL-10 (same as for selection). In brief, Maxisorb plates (Nunc, Germany) were coated with 1 µg/ml hIL-10 in PBS over night at 4° C. After blocking and washing of the plates, the supernatants of the antibody fragment producing bacteria were added. For detection of bound humanized antibody fragments a POD conjugated secondary antibody was used.

The coding sequences of good binders were analyzed and the occurrence of identified hVL- and hVH—fragments listed (Table 2).

TABLE 2

Occurrence of VL and VH fragments present in antibody fragments binding to hIL-10.

| Occurrence of variable heavy chain variants | | Occurrence of variable light chain variants | |
|---|---|---|---|
| hVH variant | Occurrence | hVL variant | Occurrence |
| hVH1 | 1 | hVL1 | 2 |
| hVH5 | 1 | hVL2 | 1 |
| hVH7 | 2 | hVL3 | 1 |
| hVH9 | 2 | hVL5 | 1 |
| hVH12 | 1 | hVL6 | 3 |
| hVH13 | 2 | hVL7 | 4 |
| hVH14 | 1 | hVL8 | 18 |
| (hVH16) | 4 | (hVL9) | 4 |
| hVH18 | 4 | hVL10 | 1 |
| hVH20 | 4 | hVL11 | 1 |
| hVH21 | 1 | hVL12 | 2 |
| hVH23 | 1 | | |
| hVH26 | 9 | | |
| hVH27 | 2 | | |
| hVH28 | 3 | | |
| hVH29 | 1 | | |

Sequences marked in bold were selected for subcloning into the appropriate eukaryotic expression vectors to analyze the binding properties in the context of the entire antibody. The sequences shown in brackets were selected for subcloning into the expression vectors but the procedure only resulted in defective constructs.

3.3 Generation of Expression Vectors for the Selected Humanized Light and Heavy Chain Variants of BT-063

Based on the statistics determined by the screening approach a set of humanized VL and humanized VH variants of BT-063 were selected for cloning into a vector system. In a first step, the cDNAs encoding the humanized VL and VH variants were transferred into an appropriate vector in order to fuse a sequence coding for a secretory signal 5' and a splice donor sequence 3' to the cloned cDNA. These cDNA constructs were, in a second and final subcloning step, transferred into the expression vectors encoding the human constant kappa and the human constant gamma-1 chain, respectively. Plasmids of independently obtained hVL and hVH containing expression vectors were prepared by the endotoxin-free Qiagen Midi-prep kit (Qiagen, Germany).

3.4 Transient Expression of the Selected Humanized BT-063 Variants in COS-7 Cells and Comparison of Antibody Binding Towards hIL-10

For the transient expression of the humanized antibody variants in COS-7 cells each of the selected humanized VL variants (hVL7 and hVL8) was combined with each of the selected humanized VH variants (hVH1, hVH9, hVH13, hVH18, hVH20, hVH26, hVH28) resulting in 14 different humanized antibodies.

In brief, the expression vectors coding for the light chain and for the heavy chain were transiently cotransfected into COS-7 cells by calcium phosphate precipitation in DMEM containing 10% FCS in a 24-well format. After transfection the medium was replaced by the serum free medium CHO-S-SFM II (Invitrogen, Germany) and the supernatants of the COS-7 cells were collected 2-3 days after transfection. The antibody titer of the humanized antibodies secreted into the supernatants of transfected COS-7 cells were analyzed by a sandwich ELISA. Based on the determined antibody concentrations supernatants of all samples were adjusted to the same antibody concentrations, and all samples were used to analyze binding to human IL-10 in an antigen ELISA, whereby Maxisorb plates (Nunc, Germany) were coated with 2 µg/ml hIL-10 in PBS.

As shown in FIG. 4, all analyzed variants bind to hIL-10, however with different binding properties. Significantly the highest signals in the antigen ELISA were obtained with the BT-063 variants hVH20/hVL7, hVH26/hVL7 and hVH20/hVL8 showing signal intensities comparable to that obtained with the chimeric B-N10 antibody. Within these three antibodies variations in signal intensities (higher signal for hVH20/hVL8 and lower signals for hVH20/hVL7 and hVH26/hVL7) could be caused by divergent antibody concentrations as a result of the quantifying sandwich ELISA (see above). All other investigated variants resulted in rather weak signals compared to the chimeric B-N10 antibody.

3.5 Production and Affinity Purification of the Chimeric and Humanized Antibody Variants The selected humanized BT-063 variants (hVH20/hVL7, hVH20/hVL8, hVH26/hVL7) and the chimeric cB-N10 (discussed in Example 2) were produced in COS-7 cells.

Transient expression was performed as described in section 3.4 whereby 10 cm tissue plates were used. Serum-free supernatants of approximately 0.5 L of each variant were collected 5 days post transfection.

Purification of the antibodies was performed by protein A affinity chromatography from serum free supernatants. Supernatants were loaded in the presence of 2M NaCl. Antibodies were eluted by a 0.1M Citrat buffer pH 4.0 and fractionated into tubes containing 2M phosphate buffer pH 7.2. Buffer exchange against PBS as well as concentration of individual antibody probes was performed by centrifugation using membranes of a 30 kDa cut off. The quality of purified materials was checked by antigen ELISA, SDS-PAGE under non-reducing as well as reducing conditions and UV measurement at 260 nm and 280 nm.

Binding towards hIL-10 of the purified chimeric B-N10 and the humanized variants was tested by ELISA according to the method as described above in Example 2. hIL10 was coated and the antibody binding was measured for the variants cB-N10, BT-063-1 (hVH20/hVL7), BT-063-2 (hVH20/hVL8) and BT-063-3 (hVH26/hVL7). The results are shown in FIG. 5.

The signal intensities were comparable for the chimeric B-N10 and the hVH20/hVL7 variant, whereas the signal intensities of the variants hVH20/hVL8 and hVH26/hVL7 were slightly less.

3.6 Affinity Determination by Biacore Human IL-10

Surface plasmon resonance analysis was used to measure the association and dissociation rate constants for binding of the different antibodies (murine, chimeric, 3 humanized variants) towards hIL-10 using BIACORE 2000 (Biacore AB, Uppsala, Sweden). hIL-10 was immobilized on a CM-5 sensor chip according to manufacturers conditions. hIL-10 was immobilized by adding a 50 µl aliquot of 20 µg/ml at a flow rate of 5 µl/minute resulting in an immobilization density of 320RU. The immobilized hIL-10 surface was regenerated in a two step cycle by using 0.1M carbonate buffer pH 9.2 and 0.01M HCL/1M NaCl at flow rates of 50 µl/minute for one minute each. Each antibody sample was analyzed at least 4 times in antibody concentration ranges of 20-0.15 µg/ml. Calculations from the sensograms were performed by using the BIA evaluation version 3 (1999) software.

Table 3 summarizes the results of all Biacore measurements. All variants bind comparable to hIL-10. However, slight differences are detectable. As a result the mouse monoclonal antibody B-N10, the chimeric cB-N10 as well as the humanized variant BT-063-1 (hVH20/hVL7) bind with comparable affinities whereas the two other humanized variants BT-063-2 (hVH20/hVL8) and BT-063-3 (hVH26/hVL7) show reduced affinities (about factor 3 compared to the murine B-N10). Slight differences in association and dissociation rates are also detectable.

TABLE 3

Results of Biacore measurements

| Antibody variant | n | ka [1/Ms] | kd [1/s] | KD [M] ± SD |
|---|---|---|---|---|
| B-N10 | 6 | 4.43E6 | 2.05E−3 | 1.07E−9 ± 3.11E−10 |
| cB-N10 | 4 | 6.23E5 | 8.48E−4 | 1.37E−9 ± 2.42E−10 |
| BT-063-1 | 6 | 1.21E6 | 1.03E−3 | 1.22E−9 ± 1.44E−10 |
| BT-063-2 | 4 | 1.21E6 | 1.64E−3 | 2.81E−9 ± 1.03E−9 |
| BT-063-3 | 5 | 1.07E6 | 2.66E−3 | 2.91E−9 ± 8.07E−10 | n = number of individual measurements;
ka = association rate;
kd = dissociation rate;
KD = dissociation constant Cynomolgus IL-10

The affinity of the BT-63 variant 3 (hVH26/hVL7) to Cynomolgus IL-10 was analysed by additional surface plasmon resonance experiments using a Biacore T100 (Biacore AB, Uppsala, Sweden).

BT-063 was diluted in 10 mM acetate pH5.5 to 5 µg/mL and immobilized using amine coupling procedure to obtain a final level of about 1000 RU. Regeneration of the sensor chip surface was obtained injecting 10 mM Glycine-HCl pH 1.8 for 30 s. Samples were injected in different concentrations over the flow cell as well as over the reference cell. Signals obtained by the reference cell were subtracted from the signals obtained by the detector flow cell and resulting binding profiles were evaluated using a 1:1 Langmuir-binding model. A concentration depending binding profile was obtained and an average KD of 194 pM was calculated for Cynomolgus IL-10. As a positive control rhIL-10 was analysed resulting in a KD of 4.6 nM. Results are summarized in Table 4.

TABLE 4

Results of Biacore measurements with BT-063

| Analyte | Assay no | ka [1/Ms] | kd [1/s] | KD [M] |
|---|---|---|---|---|
| rhIL-10 | 1 | 6.0E5 | 0.3E−2 | 4.6E−9 |
| rCIL-10 | 1 | 6.2E7 | 1.2E−2 | 0.196E−9 |

TABLE 4-continued

Results of Biacore measurements with BT-063

| Analyte | Assay no | ka [1/Ms] | kd [1/s] | KD [M] |
|---|---|---|---|---|
| rCIL-10 | 2 | 8.6E7 | 1.7E−2 | 0.195E−9 |
| rCIL-10 | 3 | 9.7E7 | 1.8E−2 | 0.191E−9 | rhIL-10: recombinant human IL-10;
rCIL-10: recombinant Cynomolgus IL-10;
ka = association rate;
kd = dissociation rate;
KD = dissociation constant Example 4

Activity of Anti-IL10 Antibodies In Vitro

To confirm the potency of BT-063, the blockade of IL-6 release in peripheral blood mononuclear cells (PBMCs) was examined. PBMCs release Interleukin-6 (IL-6) upon stimulation with Lipopolysaccharide (LPS). A physiological activity of Interleukin-10 (IL-10) is the inhibition of secretion of cytokines, e.g. IL-6. Thus, IL-10 addition to LPS stimulated cells inhibits IL-6 secretion, leading to a significant reduction of IL-6 present in the medium of the cell culture. However, as a consequence of BT-063 addition to the cell culture, IL-10 is bound and thus not able to bind to the receptor on the cell surface. The inhibitory effect of IL-10 is compensated and IL-6 secretion is restored, leading to IL-6 in the medium.

PBMCs were isolated from human blood by Ficoll gradient. The isolated cells were seeded at $1 \times 10^6$ cells/ml and stimulated with LPS for IL-6 secretion, which was inhibited by addition of IL-10. The inhibitory effect of IL-10 was neutralized by addition of BT-063, thus reconstituting IL-6 secretion. Depending on the purpose (reference or low, high quality control samples) of added BT-063, different titration concentrations of BT-063 were used, leading to concentration dependant secretion of IL-6 which were detected in the supernatant of the cell culture.

TABLE 5 mean values of IL-6 levels from double determinations and IL-6 reconstitution respectively in dependence of titration of reference standard
S1: 40 μg/mL

| concentration of BT-063 [μg/mL] | mean value of IL-6 level [μg/mL] | Reconstitution of IL-6 Secretion [%] |
|---|---|---|
| 40.000 | 42546 | 72.8% |
| 20.000 | 43134 | 73.8% |
| 13.333 | 37910 | 64.9% |
| 8.889 | 31107 | 53.2% |
| 5.926 | 25602 | 43.8% |
| 3.951 | 20793 | 35.6% |
| 1.975 | 14200 | 24.3% |
| 0.988 | 10227 | 17.5% |

As shown in Table 5, the amount of secreted IL-6 is directly correlated with the concentration of BT-063. The higher the concentration of BT-063, the more IL-6 was secreted from the PBMCs and thus present in the supernatant. Incubation of the cells with 40 μg/mL BT-063 led to a reconstitution of IL-6 secretion of about 73%, whereas with 0.988 μg/mL BT-063 (last step of titration) only 17.5% of the IL-6 level was detectable in the medium when compared to the positive control (stimulated PBMCs without IL-10 incubation).

Example 5

Different Effects of B-N10 and BT-063 on Cytokine Synthesis/Level in Human Whole Blood Cultures The immunopharmacological profile of BT-063 (variant hVH26/hVL7) was evaluated by the drug-dependent modulation of experimentally induced cytokine synthesis in human whole-blood cultures. With this method, direct and indirect influences of BT-063 on immune cell activities can be determined. BT-063 activities were compared to the effects of B-N10.

The assays utilized whole-blood cultures from both healthy volunteers and SLE patients, which were analysed for cytokine release in the presence of BT-063 or B-N10. Cytokine release by immune cells in whole blood culture was examined in a resting state after incubation with the antibodies B-N10 or BT-063, respectively. Leukocytes from healthy volunteers as well as cells from patients suffering from systemic *Lupus erythematosus* (SLE) have been included.

The cells for the experiments described in the following were obtained by simple bleeding of the volunteers or the SLE patients and their incubation with BT-063 or B-N10 respectively was done for 2 days in microculture plates.

The mediators measured in these experiments were mainly cytokines and chemokines, associated for example with Th-1-, Th-2- or monocyte/macrophage-activation, such as Interferon gamma (IFN-gamma), interleukin-1 beta (IL-1beta), IL-12, IL-4, IL-8, or tumor necrosis factor alpha (TNF-alpha). The concentration of each parameter to be tested in the culture supernatants were determined using a multiparametric bead-based readout system (Luminex™-based technology, called multi-analyte profile, or MAP, tests Rules-Based Medicine, RBM (Austin, Tex., USA).). These assays were performed by EDI GmbH, Reutlingen, Germany The Luminex™ technology works in a manner similar to a mixture between ELISA and flow cytometry and counts 100 beads per analyte, so the individual concentrations are back-calculated from the mean fluorescence intensity of 100 individual measurements.

Only at antibody concentrations of 50 μg/ml, an induction of cytokine release has been observed.

Absolute cytokine levels measured in cell cultures from healthy donors and from SLE patients incubated with B-N10 or BT-063 are summarized in Tables 6 and 7 below.

TABLE 6

Summary of the cytokines which are differentially regulated by B-N10 or BT-063 in whole blood cultures of healthy donors. Absolute values of cytokines +/− SD (in ng/ml for IL1 alpha, MMP-2, in pg/ml for all other cytokines) released after incubation with 50 μg/ml antibody concentrations.
Healthy volunteers
induced in unstimulated cultures at 50 μg/ml

| | BT063 Mean | +/−SD | B-N10 Mean | +/−SD |
|---|---|---|---|---|
| | T cell cytokines | | | |
| IFN gamma | 24 | 15 | 1757 | 1545 |
| IL-2 | 0 | 0 | 19 | 12 |
| IL-17 | 20 | 4 | 116 | 51 |
| IL-4 | 22 | 4 | 96 | 4 |

TABLE 6-continued

Summary of the cytokines which are differentially regulated by
B-N10 or BT-063 in whole blood cultures of healthy donors.
Absolute values of cytokines +/− SD (in ng/ml for IL1 alpha,
MMP-2, in pg/ml for all other cytokines) released after incubation
with 50 μg/ml antibody concentrations.
Healthy volunteers
induced in unstimulated cultures at 50 μg/ml

| | BT063 Mean | +/−SD | B-N10 Mean | +/−SD |
|---|---|---|---|---|
| T cell survival | | | | |
| IL-7 | 103 | 15 | 319 | 31 |
| Chemokines | | | | |
| Mip1-beta | 5453 | 852 | 316667 | 134656 |
| Mip1-alpha | 154 | 34 | 6227 | 5763 |
| MCP-1 | 1852 | 1001 | 120933 | 30897 |
| IL-8 | 2093 | 266 | 65967 | 26515 |
| Proinflammatory cytokines | | | | |
| IL-6 | 20 | 2 | 20400 | 11557 |
| IL1-alpha | 0.133 | 0.008 | 0.356 | 0.142 |
| IL1 beta | 44 | 16 | 3160 | 2936 |
| TNF alpha | 24 | 9 | 1068 | 386 |
| Anti-inflammatory | | | | |
| IL-10 | 3 | 1 | 146 | 62 |

TABLE 7

Summary of differentially regulated cytokines (absolute
values) by B-N10 or BT-063 in whole blood cultures of SLE
patients. Absolute values of cytokines (in ng/ml for IL1
alpha, MMP-2, in pg/ml for all other cytokines) released
after incubation with 50 μg/ml antibody concentrations.

| | BT063 Mean | +/− | B-N10 Mean | +/− |
|---|---|---|---|---|
| T cell cytokines | | | | |
| IFNgamma | 1 | 1 | 323 | 407 |
| IL-2 | 0 | 0 | 17 | 5 |
| IL-4 | 28 | 1 | 118 | 80 |
| IL-17 | 16 | 13 | 75 | 91 |
| T cell survival | | | | |
| IL-7 | 75 | 11 | 290 | 166 |
| Chemokines | | | | |
| IL-8 | 8410 | 9744 | 121100 | 145523 |
| Mip1 alpha | 100 | 9 | 10235 | 12961 |
| Mip1 beta | 3695 | 1407 | 156350 | 82944 |
| MCP-1 | 2580 | 2560 | 600500 | 663973 |
| ProInflammatory cytokines | | | | |
| IL-6 | 227 | 284 | 23200 | 17253 |
| IL1-beta | 69 | 27 | 1420 | 438 |
| Anti-inflammatory | | | | |
| IL-10 | 8410 | 9744 | 121100 | 145523 |
| IL-1 alpha | 0.072 | 0.048 | 0.206 | 0.013 |
| TNF alpha | 7 | 0 | 572 | 200 |
| TNF beta | 0 | 0 | 66 | 42 |
| Matrix metallo proteinases | | | | |
| MMP-2 | 27 | 12 | 365 | 203 |

FIGS. 6A and B, 7A and B, 8A and B, and 9A and B show the differential regulation of proinflammatory cyokines in human whole blood cultures from both healthy volunteers and SLE patients under non-stimulating conditions. The figures show that whole blood cultures from healthy volunteers and SLE patients display higher TNFalpha, IL-6, IL-1beta and IFN-gamma release after incubation with B-N10 compared to BT-063 (at 50 μg/ml). It is noted that besides the proinflammatory function IL-6 acts in addition as factor for B-cell differentiation into plasma cells. Remarkably it can be seen from these results that IL-10 and pro-inflammatory cytokines are upregulated to a higher extent by B-N10 compared to BT-063 incubated cultures from both healthy and SLE donors, suggesting a better safety profile. This would be not expected as a result upon humanization procedure.

Example 6

X-Ray Crystallography 6.1 Crystallisation of BT-063 Fab in Complex with Human IL-10

Several constructs of IL-10 were designed according to published structural data (Zdanov et al., Structure, Vol. 3, 1995, pp. 591) and cloned by standard procedures into vectors for heterologous expression in *E. coli*. Test expressions of the cloned constructs were performed according to standard protocols and showed a high over-expression for IL-10 as indicated by an increase in a band in the expected range of around 18 kDa.

IL-10 protein expressed under optimised conditions yielded viable amounts for subsequent protein purification. After refolding, the protein was purified by immobilised affinity chromatography, size exclusion chromatography and ion exchange chromatography to yield protein with over 95% homogeneity as judged by Coomassie-stained SDS-PAGE. The yield of purified protein was approximately 0.3 mg per litre expression culture, which was sufficient for crystallisation trials.

The Fab fragment of BT-063 (variant hVH26/hVL7) was cleaved from the intact antibody using the protease papain and purified by protein A. Subsequently the Fab fragment was further purified by size exclusion chromatography.

The IL-10:BT-063 Fab complex was formed by mixing the purified proteins, with a molar excess of IL-10 and further purification by size exclusion chromatography. The retention volume was consistent with the size of the complex.

The protein was subsequently concentrated to concentrations suitable for crystallisation.

Crystals of the IL-10:BT-063 Fab complex were prepared by the method of co-crystallisation.

6.2 Data Collection and Processing

Crystals were flash-frozen and measured at a temperature of 100 K. The X-ray diffraction data have been collected from co-crystals of IL-10 with the Fab fragment of BT-063 at the SWISS LIGHT SOURCE (SLS, Villigen, Switzerland) using cryogenic conditions.

The crystals belong to space group P6 with two complexes in the asymmetric unit. Data were processed using the programmes XDS and XSCALE. Data collection statistics are summarised in Table 8.

TABLE 8

Statistics of data collection and processing

| Complex | IL-10:BT-063 |
|---|---|
| X-ray source | PX (SLS[1]) |
| Wavelength [Å] | 1.0007 |
| Detector | PILATUS |
| Temperature [K] | 100 |
| Space group | P 6 |

TABLE 8-continued

Statistics of data collection and processing

| Complex | IL-10:BT-063 |
|---|---|
| Cell: a; b; c [Å] | 219.00; 219.00; 64.36 |
| α; β; γ [°] | 90.0; 90.0; 120.0 |
| Resolution [Å][2] | 3.48 (3.72-3.48) |
| Unique reflections[2] | 21124 (3817) |
| Multiplicity[2] | 3.0 (2.9) |
| Completeness [%][2] | 91.2 (92.3) |
| $R_{sym}$[%][2, 3] | 10.5 (44.0) |
| $R_{meas}$[%][2, 4] | 14.8 (62.2) |
| I/σ I[2] | 6.1 (1.7) |
| mean(I)/sigma[2, 5] | 7.0 (1.7) |

[1]SWISS LIGHT SOURCE (SLS, Villigen, Switzerland)
[2]Numbers in brackets correspond to the highest resolution bin.

$$^3R_{sym} = \frac{\sum_h \sum_i^{n_h} |\hat{I}_h - I_{h,i}|}{\sum_h \sum_i^{n_h} I_{h,i}} \text{ with } \hat{I}_h = \frac{1}{n_h}\sum_i^{n_h} I_{h,i}$$

where $I_{h,i}$ is the intensity value of the ith measurement of h $$^4R_{meas} = \frac{\sum_h \sqrt{\frac{n_h}{n_h-1}} \sum_i^{n_h} |\hat{I}_h - I_{h,i}|}{\sum_h \sum_i^{n_h} I_{h,i}} \text{ with } \hat{I}_h = \frac{1}{n_h}\sum_i^{n_h} I_{h,i}$$

where $I_{h,i}$ is the intensity value of the ith measurement of h
[5]Calculated from independent reflections

6.3 Structure Modelling and Refinement

The phase information necessary to determine and analyse the structure was obtained by molecular replacement. Published models of IL-10 and a Fab fragment were used as a search model. Subsequent model building and refinement was performed according to standard protocols with the software packages CCP4 and COOT. For the calculation of the free R-factor, a measure to cross-validate the correctness of the final model, 4.2% of measured reflections were excluded from the refinement procedure (see Table 9).

The nanobody parameterisation was carried out with the programme CHEMSKETCH. LIBCHECK (CCP4) was used for generation of the corresponding library files.

The water model was built with the "Find waters . . . "-algorithm of COOT by putting water molecules in peaks of the Fo-Fc map contoured at 3.0σ followed by refinement with REFMAC5 and checking all waters with the validation tool of COOT. The criteria for the list of suspicious waters were: B-factor greater 80, 2Fo-Fc map less than 1.2σ, distance to closest contact less than 2.3 Å or more than 3.5 Å. The suspicious water molecules and those in the active site (distance to inhibitor less than 10 Å) were checked manually. The occupancy of side chains, which were in negative peaks in the Fo-Fc map (contoured at −3.0σ), were set to zero and subsequently to 0.5 if a positive peak occurred after the next refinement cycle.

The Ramachandran Plot of the final model shows 80.8% of all residues in the most favoured region, 17.9% in the additionally allowed region, 0.7% of the residues in the generously allowed. Residues Val86(A), His14(B), Asp86(B), Ser131(C), Val56(D) and Val56(F) are found in the disallowed region of the Ramachandran plot (Table 9). They are either confirmed by the electron density map or could not be modelled in another sensible conformation. Statistics of the final structure and the refinement process are listed in Table 9.

TABLE 9

Refinement statistics[1]

| Complex | IL-10:BT-063 |
|---|---|
| Resolution [Å] | 20.0-3.48 |
| Number of reflections (working/test) | 20199/889 |
| $R_{cryst}$[2] [%] | 29.7 |
| $R_{free}$[2] [%] | 35.5 |
| Total number of atoms: | |
| Protein | 8870 |
| Water | |
| Ligand | — |
| Deviation from ideal geometry:[3] | |
| Bond lengths [Å] | 0.007 |
| Bond angles [°] | 0.93 |
| Bonded B's[4] [Å²] | 0.0 |
| Ramachandran Plot:[5] | |
| Most favoured regions | 80.8 |
| Additional allowed regions | 17.9 |
| Generously allowed regions | 0.7 |
| Disallowed regions | 0.6 |

[1]Values as defined in REFMAC5, without sigma cut-off
[2]Test-set contains 4.2% of measured reflections
[3]Root mean square deviations from geometric target values
[4]Calculated with programme MOLEMAN
[5]Calculated with programme PROCHECK

6.4 X-Ray Structure Analysis

The complex structure of human IL-10 bound by BT-063 Fab antibody fragment was analysed at a resolution of 3.48 Å and reveals the detailed binding mode of the Fab antibody fragment.

The resulting electron density shows an unambiguous binding mode for the Fab fragment, including the orientation and conformation of the Fab fragment. The crystal of space group P6 contains two complexes in the asymmetric unit.

The structure of IL-10 in complex with Fab is represented in FIG. 6. Two Fab fragments bind with their CDR loops to each homodimer of IL-10.

The following residues of IL-10 (molecules A and B) can be found in the vicinity of the CDR loops within a maximum distance of 3.9 Å: Arg27, Lys 34, Gln38, Met39, Asp41, Gln42, Asp44, Leu46, Glu50, Leu53, Glu142, Asp144, Ile145, Asn148, Tyr149, Glu151, and Thr155.

The following residues of the CDR loops can be found in the vicinity of the IL-10 within a maximum distance of 3.9 Å: Phe27, Ser28, Ala30, Thr31, Tyr32, Trp52, Arg53, Gly54, Ser56, Asn73, Ser74, Tyr100, Gly101, Tyr103 (molecules C and E), Ser32, Asn33, Asn35, Tyr37, Lys55 (molecules D and F).

The binding site of BT-063 coincides with the binding site of the IL-10 receptor on the surface of IL-10 as shown by overlaying the complex structure of IL-10:BT-063 with a published structure of the IL-10:IL-10R1 receptor complex (FIG. 7).

The BT-063 amino acid residues in contact with human IL-10 as identified by X-ray analysis are highlighted on the linear amino acid sequence of BT-063 variable antibody domains shown below.

```
BT-063 VL
                                                      (SEQ ID No: 69)
DVVMTQSPLS  LPVTLGQPAS  ISCRSSQNIV  HSNGNTYLEW

YLQRPGQSPR  LLIYKVSNRF  SGVPDRFSGS  GSGTDFTLKI

SRVEAEDVGV  YYCFQGSHVP  WTFGQGTKVE  IK

BT-063 VH:
                                                      (SEQ ID No: 70)
EVQLVESGGG  LVQPGGSLRL  SCAASGFSFA  TYGVHWVRQS

PGKGLEWLGV  IWRGGSTDYS  AAFMSRLTIS  KDNSKNTVYL

QMNSLRAEDT  AVYFCAKQAY  GHYMDYWGQG  TSVTVSS
```

CDR regions (Honegger and Plückthun (2001) J. Mol. Biol., 309, 657-670) are underlined (CDR1, CDR2 and CDR3 of the light chain are SEQ ID Nos: 71, 72 and 73, respectively; CDR1, CDR2 and CDR3 of the heavy chain are SEQ ID Nos: 74, 75 and 76, respectively). Contact residues with IL-10 are shown in bold.

Within the light chain contact residues are found in CDR1 and CDR2 but not in CDR3. Regarding the heavy chain resides of all three CDRs are involved in antigen binding. Two residues of FR3 (Asn73 and Ser74) also contribute to antigen binding.

Ser28 and Ala30 at the beginning of CDR1 are part of the murine VH predecessor sequence (BN-10) and not present in the selected human framework (3-66*04). Both positions are less frequently involved in antigen binding and were introduced as alternative amino acids during the humanisation process.

Residues Asn73 and Ser74 are found in murine and frequently in human antibody framework sequences but are usually not involved in antigen binding. (www.bioc.uzh.ch/antibody; Honegger and Plückthun, 2001). Their contribution to antigen binding is unexpected.

IL-10 amino acid residues involved in BT-063 binding are shown below. Also indicated are residues of IL-10 involved in binding to the high affinity IL-10 receptor chain (IL-10R1) and the low affinity receptor chain (IL-10R2). Both receptor chains are involved in the binding of a IL-10 homodimer and necessary for signaling. In sequence A the residues which contact BT-063 are shown in bold. In sequence B the contact residues to IL-10R1 are marked in bold, contact residues to IL-10R2 are marked in italics and underlined and contact residues shared by IL-10R1 and 2 are marked in as being in bold, italics and underlined (Pletnev et al 2005).

```
A
                                                                (SEQ ID NO: 1)
SPGQGTQSEN SCTHFPGNLP NMLRDLRDAF SRVKTFFQMK DQLDNLLLKE SLLEDFKGYL

GCQALSEMIQ FYLEEVMPQA ENQDPDIKAH VNSLGENLKT LRLRLRRCHR FLPCENKSKA

VEQVKNAFNK LQEKGIYKAM SEFDIFINYI EAYMTMKIRN

B
                                                                (SEQ ID NO: 1)
SPGQGTQSEN SCTHFPGNLP NMLRDLRDAF SRVKTFFQMK DQLDNLLLKE SLLEDFKGYL

GCQALSEMIQ FYLEEVMPQA ENQDPDIKAH VNSLGENLKT LRLRLRRCHR FLPCENKSKA

VEQVKNAFNK LQEKGIYKAM SEFDIFINYI EAYMTMKIRN
```

It can be seen that BT-063 binds to a discontinuous epitope of IL-10 comprising residues of helix A (Arg27, Lys34, Gln38, Met39, Asp41) and the N-terminal part of helix B (Glu50 and Leu53) including the connecting loop sequence (Glu42, Asp44, Leu46) of one IL-10 monomer as well as residues of the helix F' (Glu142, Asp144, Ile145, Asn148, Tyr149, Glu151, Thr155) of the second IL-10 monomer.

Example 7

In Vivo Single Dose Toxicity Study in Cynomolgous Monkey

A single dose toxicity study including safety pharmacology parameters was performed in Cynomolgus monkeys following a single intravenous injection of BT-063 (variant hVH26/hVL7). Animals were distributed into four groups (placebo, 1 mg/kg, 7 mg/kg and 50 mg/kg) with 4 animals/sex/group. BT-063 was intravenously injected on day 1. Half of the animals were necropsied after 5 days, while the remaining animals were sacrificed on day 28.

The low dose level of 1 mg/kg in this study corresponds to a human equivalent dose of ~300 μg/kg, resulting in a total human dose of 18 mg (60 kg body weight). A similar dose of the BT-063 predecessor antibody B-N10 had been applied daily for 21 days in a small investigator initiated trial (Llorente, 2000). This amount of antibody has shown pharmacological effects and clinical efficacy. The low dose level was therefore chosen accordingly. The high dose was chosen as a multiple (50 μg) of the starting dose. The intermediate dose is the geometric mean of the low and the high doses.

During the study no toxicologically significant or relevant changes in physiological or histopathology parameters were observed. In addition, changes in clinical chemistry parameters were considered of little or no toxicological significance.

Example 8

In Vivo Single Dose Toxicity Study in Healthy Volunteers

A study was conducted to monitor the safety and tolerability of BT-063 (variant hVH26/hVL7), and the effects of BT-063 administration, using escalating doses of the antibody in healthy volunteers. Twenty-three volunteers received a single intravenous administration of BT-063, in 8 dosage groups. The dosage groups were as follows: 0.175 mg, 0.75 mg, 3.5 mg, 7 mg, 15 mg, 30 mg, 60 mg and 100 mg. There were three volunteers per group, except for the 100 mg dose group where there were two volunteers.

Each dose was diluted with 0.9% sodium chloride injection up to a total volume of 20 ml. The dose is administered as a single continuous intravenous infusion over 2 hours.

The volunteers were assessed over a period of 85 days after the injection and blood was taken at multiple time points over this period.

Cytokines

From the plasma taken, assessments were made on the levels of cytokines IFNγ, IL-1β, IL-2, IL-4, IL-5, IL-6, IL-8, IL-10 and TNFα before and after infusion of BT-063.

Table 10 shows the upper limit of normal values for IL-6, IL-8 and IL-10 calculated from predose and screening values.

TABLE 10

Cytokine concentration in healthy volunteers

|  | Cytokine (pg/mL) | | |
| --- | --- | --- | --- |
|  | IL-6 | IL-8 | IL-10 |
| Mean | 5.6 | 12.4 | 4.9 |
| SD | 10.6 | 11.5 | 9.3 |
| ULN (Mean + 2 × SD) | 26.7 | 35.3 | 23.5 |
| Range (lowest to highest values) | 0-44.5 | 0.0-45.1 | 0.0-40.2 |

Further results from the cytokine measurements are shown in FIGS. 12 and 13.

A non-dose dependent transient increase of IL-6 and IL-8 was present within the 24 hours post infusion, returning to pre-dose levels after 3 days. This effect is thought to be associated with the infusion event rather than with the antibody since there was no dose relationship and the effect occurred already at the lowest dose Surprisingly, given that IL-10 is an important regulatory cytokine, no increase in levels of IFNγ, IL-1β, IL-2, IL-4, IL-5, and TNFα were detected as shown in FIG. 12. The lack of elevation in levels of IL-4, IL-5 IFN-γ, IL-2 also confirm that there is no T-helper cell activation resulting from the BT-063 administration. Further, since body temperature is also an indication of the large-scale release of pro-inflammatory cytokines, this parameter was also measured in the treated volunteers. However, no increase in body temperature was detected after administration.

As shown in FIG. 13, only IL-10 plasma concentration is influenced by administration of BT-063, with detected plasma IL-10 increasing as the dose of BT-063 is increased. It is noted that the assay used detects both free IL-10 and IL-10 bound to BT-063. There are two possible explanations for the increase: (1) a prolonged half life of IL-10, with binding of IL-10 to BT-063 preventing IL-10 internalization, and concomitantly no elimination of IL-10 from the blood (there is normally a rapid turnover of IL-10, with the half life of secreted IL-10 being approximately 2.3-3.5 hours (Huhn et al., Blood (1996) January 15: 87(2): 699-705)); and/or (2) induction of a negative feedback loop—with BT-063 blocking the binding of IL-10 to its receptor no cellular uptake of IL-10 is possible, triggering B-cells to produce more IL-10. We consider that scenario (2) is more probable since it is confirmed by in vitro data taken from whole blood culture experiments with BT-063 and murine IL-10R knockout cells (Mahnke et al., unpublished data).

Pharmacokinetics

The pharmacokinetic data showed that the Cmax, AUC and half-life of BT-063 are in the range of the expected theoretical values. The terminal half-life of BT-063 being between 15 and 30 days. After administration of doses of 30 mg or higher, BT-063 is still detectable in the plasma after 85 days.

No human anti-human antibodies (HAHA) were observed in the treated volunteers, despite the fact that HAHA responses have been observed with other cytokine neutralizing antibodies (e.g. with Adalimumab, a humanized anti-TNF alpha).

Despite the increase in detected amounts of IL-10 after administration of BT-063 it is noted that this study demonstrates the safety and tolerability of even large dosages of BT-063 and thus it can be concluded that sufficient dosages of BT-063 can be safely administered (in particular, the absence of an intolerable increase in the level of pro-inflammatory cytokines) to SLE patients to counteract the effects of excess IL-10.

The invention claimed is:

1. A humanized or chimeric antibody or fragment thereof capable of binding to interleukin-10 (IL-10), wherein said antibody or fragment thereof comprises a variable light chain comprising the amino acid sequences of SEQ ID NO: 71, 72 and 73, and a variable heavy chain comprising the amino acid sequences SEQ ID NO: 74, 75 and 76.

2. A humanized or chimeric antibody or fragment thereof according to claim 1, wherein the antibody or fragment thereof comprises at least one of the variable light chain of SEQ ID NO: 69 or the variable heavy chain of SEQ ID NO: 70.

3. A humanized or chimeric antibody or fragment thereof according to claim 1 wherein the antibody or fragment thereof comprises the variable light chain of SEQ ID NO: 69 and the variable heavy chain of SEQ ID NO: 70.

4. A nucleic acid encoding the antibody or fragment thereof of claim 1.

5. A vector comprising a nucleic acid according to claim 4.

6. A host cell comprising a nucleic acid according to claim 4.

7. A method for the production of an antibody or a fragment thereof according to claim 1, comprising a step of culturing a host cell comprising a nucleic acid that encodes said antibody or fragment thereof in a culture medium under conditions allowing the expression of the antibody or fragment thereof and separating the antibody or fragment from the culture medium.

8. A pharmaceutical composition comprising the antibody or fragment thereof according to claim 1, and further comprising a pharmaceutically acceptable carrier.

9. A method for treating a medical condition in a subject, wherein the medical condition is mediated by an elevated level or activity of IL-10, comprising administering a therapeutically effective amount of an antibody or fragment thereof according to claim 1 to said subject.

10. A method for treating a medical condition in a subject, wherein the medical condition is mediated by an elevated level or activity of IL-10, comprising administering a therapeutically effective amount of an antibody or fragment thereof according to claim 1 to said subject, wherein the subject is not simultaneously or separately treated with a corticosteroid.

11. A method of treating a medical condition in a subject according to claim 9 wherein the medical condition is systemic lupus erythematosus (SLE).

12. A labeled antibody or fragment thereof comprising the antibody or fragment thereof according to claim 1 and a label.

13. A humanized or chimeric antibody according to claim 1 further comprising an IgG1 constant domain.

14. A humanized or chimeric antibody comprising a variable light chain having SEQ ID NO: 69, a variable heavy chain having SEQ ID NO: 70, and an IgG1 constant domain.

\* \* \* \* \*

SEQUENCE LISTING

```
<160> NUMBER OF SEQ ID NOS: 76

<210> SEQ ID NO 1
<211> LENGTH: 160
<212> TYPE: PRT
<213> ORGANISM: Human

<400> SEQUENCE: 1

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Val Met Pro Gln Ala
65                  70                  75                  80

Glu Asn Gln Asp Pro Asp Ile Lys Ala His Val Asn Ser Leu Gly Glu
```

```
            85                  90                  95
Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
            130                 135                 140

Ile Phe Ile Asn Tyr Ile Glu Ala Tyr Met Thr Met Lys Ile Arg Asn
145                 150                 155                 160

<210> SEQ ID NO 2
<211> LENGTH: 114
<212> TYPE: PRT
<213> ORGANISM: Mus musculus

<400> SEQUENCE: 2

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Leu Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Ala

<210> SEQ ID NO 3
<211> LENGTH: 116
<212> TYPE: PRT
<213> ORGANISM: Mus musculus

<400> SEQUENCE: 3

Gln Val Gln Leu Lys Gln Ser Gly Pro Gly Leu Leu Gln Pro Ser Gln
1               5                   10                  15

Ser Leu Ser Ile Ser Cys Thr Val Ser Gly Phe Ser Leu Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser
        115

<210> SEQ ID NO 4
```

<210> SEQ ID NO 4
<211> LENGTH: 16
<212> TYPE: PRT
<213> ORGANISM: Mus musculus

<400> SEQUENCE: 4

Arg Ser Ser Gln Asn Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Val Pro Trp Thr
1               5

<210> SEQ ID NO 7
<211> LENGTH: 5
<212> TYPE: PRT
<213> ORGANISM: Mus musculus

<400> SEQUENCE: 7

Thr Tyr Gly Val His
1               5

<210> SEQ ID NO 8
<211> LENGTH: 16
<212> TYPE: PRT
<213> ORGANISM: Mus musculus

<400> SEQUENCE: 8

Val Ile Trp Arg Gly Gly Ser Thr Asp Tyr Ser Ala Ala Phe Met Ser
1               5                   10                  15

<210> SEQ ID NO 9
<211> LENGTH: 9
<212> TYPE: PRT
<213> ORGANISM: Mus musculus

<400> SEQUENCE: 9

Gln Ala Tyr Gly His Tyr Met Asp Tyr
1               5

<210> SEQ ID NO 10
<211> LENGTH: 342
<212> TYPE: DNA
<213> ORGANISM: Mus musculus

<400> SEQUENCE: 10
gatgttttga tgacccaaac tccactctcc ctgcctgtca gtcttggaga tcaagcctcc        60
atctcttgca gatctagtca gaacattgta catagtaatg aaacaccta tttagaatgg        120 tacctgcaga aaccaggcca gtctccaaag ctcctgatct acaaagtttc caaccgattt       180
tctggggtcc cagacaggtt cagtggcagt ggatcaggga cagatttcac actcaagatc       240

```
accagattgg aggctgagga tctgggagtt tattactgct ttcaaggttc acatgttccg    300
tggacgttcg gtggaggcac caagctggaa atcaaacggg cc                      342
```

<210> SEQ ID NO 11
<211> LENGTH: 348
<212> TYPE: DNA
<213> ORGANISM: Mus musculus

<400> SEQUENCE: 11

```
caggtgcagc tgaagcagtc aggacctggc ctactgcagc cctcacagag cctgtccata    60
tcctgcacag tctctggttt ctcattagct acctatggtg tacactgggt tcgccagtct   120
ccaggaaagg gtctggagtg gctgggagtg atttggagag gtgggagcac agactacagt   180
gcagctttca tgtccagact gagcatcacc aaggacaact ccaagagcca agttttcttt   240
aaaatgaaca gtctgcaagc tgatgacact gccatttact tctgtgccaa acaggcgtat   300
ggtcactaca tggactactg gggtcaagga acctcagtca ccgtctcc                348
```

<210> SEQ ID NO 12
<211> LENGTH: 112
<212> TYPE: PRT
<213> ORGANISM: Mus musculus

<400> SEQUENCE: 12

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Leu Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 13
<211> LENGTH: 117
<212> TYPE: PRT
<213> ORGANISM: Mus musculus

<400> SEQUENCE: 13

```
Gln Val Gln Leu Lys Gln Ser Gly Pro Gly Leu Leu Gln Pro Ser Gln
1               5                   10                  15

Ser Leu Ser Ile Ser Cys Thr Val Ser Gly Phe Ser Leu Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Phe Cys Ala
                85                  90                  95
```

```
Lys Gln Ala Tyr Gly His Tyr Met Asp Tyr Trp Gly Gln Gly Thr Ser
                100                 105                 110

Val Thr Val Ser Ser
        115

<210> SEQ ID NO 14
<211> LENGTH: 100
<212> TYPE: PRT
<213> ORGANISM: Human

<400> SEQUENCE: 14

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 15
<211> LENGTH: 12
<212> TYPE: PRT
<213> ORGANISM: Human

<400> SEQUENCE: 15

Trp Thr Phe Gly Gln Gly Thr Lys Val Glu Ile Lys
1               5                   10

<210> SEQ ID NO 16
<211> LENGTH: 97
<212> TYPE: PRT
<213> ORGANISM: Human

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 17
<211> LENGTH: 15
<212> TYPE: PRT
```

<213> ORGANISM: Human

<400> SEQUENCE: 17

Tyr Phe Asp Tyr Trp Gly Gln Gly Thr Leu Val Thr Val Ser Ser
1               5                   10                  15

<210> SEQ ID NO 18
<211> LENGTH: 112
<212> TYPE: PRT
<213> ORGANISM: Artificial Sequence
<220> FEATURE:
<223> OTHER INFORMATION: hVL1

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: hVL2

<400> SEQUENCE: 19

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: hVL3

<400> SEQUENCE: 20

Asp Val Val Met Thr Gln Thr Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: hVL4

<400> SEQUENCE: 21

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: hVL5

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

```
Ser His Val Pro Trp Thr Phe Gly Gln Gly Thr Lys Val Glu Ile Lys
            100                 105                 110
```

<210> SEQ ID NO 23
<211> LENGTH: 112
<212> TYPE: PRT
<213> ORGANISM: Artificial Sequence
<220> FEATURE:
<223> OTHER INFORMATION: hVL6

<400> SEQUENCE: 23

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110
```

<210> SEQ ID NO 24
<211> LENGTH: 112
<212> TYPE: PRT
<213> ORGANISM: Artificial Sequence
<220> FEATURE:
<223> OTHER INFORMATION: hVL7

<400> SEQUENCE: 24

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 25
<211> LENGTH: 112
<212> TYPE: PRT
<213> ORGANISM: Artificial Sequence
<220> FEATURE:
<223> OTHER INFORMATION: hVL8

<400> SEQUENCE: 25

```
Asp Val Leu Met Thr Gln Ser Pro Leu Ser Leu Pro Val Thr Leu Gly
1               5                   10                  15
```

```
Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 26
<211> LENGTH: 112
<212> TYPE: PRT
<213> ORGANISM: Artificial Sequence
<220> FEATURE:
<223> OTHER INFORMATION: hVL9

<400> SEQUENCE: 26

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: hVL10

<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: hVL11

<400> SEQUENCE: 28

Asp Val Val Met Thr Gln Thr Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Thr Lys Val Glu Ile Lys
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: hVL12

<400> SEQUENCE: 29

Asp Val Val Met Thr Gln Thr Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 30
<211> LENGTH: 117
<212> TYPE: PRT
<213> ORGANISM: Artificial Sequence
<220> FEATURE:
<223> OTHER INFORMATION: hVH1

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
            85                  90                  95

Arg Gln Ala Tyr Gly His Tyr Met Asp Tyr Trp Gly Gln Gly Thr Leu
            100                 105                 110

Val Thr Val Ser Ser
            115

<210> SEQ ID NO 31
<211> LENGTH: 117
<212> TYPE: PRT
<213> ORGANISM: Artificial Sequence
<220> FEATURE:
<223> OTHER INFORMATION: hVH2

<400> SEQUENCE: 31

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Ser Phe Ala Thr Tyr
            20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
            85                  90                  95

Arg Gln Ala Tyr Gly His Tyr Met Asp Tyr Trp Gly Gln Gly Thr Leu
            100                 105                 110

Val Thr Val Ser Ser
            115

<210> SEQ ID NO 32
<211> LENGTH: 117
<212> TYPE: PRT
<213> ORGANISM: Artificial Sequence
<220> FEATURE:
<223> OTHER INFORMATION: hVH3

<400> SEQUENCE: 32

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Tyr
            20                  25                  30

Gly Val His Trp Val Arg Gln Ser Pro Gly Lys Gly Leu Glu Trp Val
            35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
            85                  90                  95

-continued

Arg Gln Ala Tyr Gly His Tyr Met Asp Tyr Trp Gln Gly Thr Leu
            100                 105                 110

Val Thr Val Ser Ser
        115

<210> SEQ ID NO 33
<211> LENGTH: 117
<212> TYPE: PRT
<213> ORGANISM: Artificial Sequence
<220> FEATURE:
<223> OTHER INFORMATION: hVH4

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 34
<211> LENGTH: 117
<212> TYPE: PRT
<213> ORGANISM: Artificial Sequence
<220> FEATURE:
<223> OTHER INFORMATION: hVH5

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Leu Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 35
<211> LENGTH: 117
<212> TYPE: PRT

```
<213> ORGANISM: Artificial Sequence
<220> FEATURE:
<223> OTHER INFORMATION: hVH6

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: hVH7

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: hVH8

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
50                  55                  60

Ser Arg Phe Thr Ile Ser Arg Asp Asn Ser Lys Asn Thr Leu Tyr Phe
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
                100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: hVH9

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Leu
                100                 105                 110

Val Thr Val Ser Ser
        115

<210> SEQ ID NO 39
<211> LENGTH: 117
<212> TYPE: PRT
<213> ORGANISM: Artificial Sequence
<220> FEATURE:
<223> OTHER INFORMATION: hVH10

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala

```
                    85                  90                  95
Lys Gln Ala Tyr Gly His Tyr Met Asp Tyr Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: hVH11

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Ser
            100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: hVH12

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 42
<211> LENGTH: 117
```

```
<212> TYPE: PRT
<213> ORGANISM: Artificial Sequence
<220> FEATURE:
<223> OTHER INFORMATION: hVH13

<400> SEQUENCE: 42
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

```
<210> SEQ ID NO 43
<211> LENGTH: 117
<212> TYPE: PRT
<213> ORGANISM: Artificial Sequence
<220> FEATURE:
<223> OTHER INFORMATION: hVH14

<400> SEQUENCE: 43
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Leu
            100                 105                 110

Val Thr Val Ser Ser
        115

```
<210> SEQ ID NO 44
<211> LENGTH: 117
<212> TYPE: PRT
<213> ORGANISM: Artificial Sequence
<220> FEATURE:
<223> OTHER INFORMATION: hVH15

<400> SEQUENCE: 44
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr

-continued

```
                20                  25                  30
Gly Val His Trp Val Arg Gln Ser Pro Gly Lys Gly Leu Glu Trp Leu
            35                  40                  45
Gly Val Ile Trp Arg Gly Gly Ser Thr Asp Tyr Ser Ala Ala Phe Met
        50                  55                  60
Ser Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Phe Cys Ala
                85                  90                  95
Lys Gln Ala Tyr Gly His Tyr Met Asp Tyr Trp Gly Gln Gly Thr Ser
            100                 105                 110
Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: hVH16

<400> SEQUENCE: 45

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
                20                  25                  30
Gly Val His Trp Val Arg Gln Ala Pro Gly Lys Gly Leu Glu Trp Val
            35                  40                  45
Ser Val Ile Trp Arg Gly Gly Ser Thr Asp Tyr Ser Ala Ala Phe Met
        50                  55                  60
Ser Arg Phe Thr Ile Ser Arg Asp Asn Ser Lys Asn Thr Leu Tyr Phe
65                  70                  75                  80
Gln Met Asn Ser Leu Arg Ala Glu Asp Thr Ala Val Tyr Phe Cys Ala
                85                  90                  95
Lys Gln Ala Tyr Gly His Tyr Met Asp Tyr Trp Gly Gln Gly Thr Leu
            100                 105                 110
Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: hVH17

<400> SEQUENCE: 46

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
                20                  25                  30
Gly Val His Trp Val Arg Gln Ala Pro Gly Lys Gly Leu Glu Trp Leu
            35                  40                  45
Gly Val Ile Trp Arg Gly Gly Ser Thr Asp Tyr Ser Ala Ala Phe Met
        50                  55                  60
Ser Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Val Tyr Tyr Cys Ala
            85                  90                  95

Lys Gln Ala Tyr Gly His Tyr Met Asp Tyr Trp Gly Gln Gly Thr Ser
        100                 105                 110

Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: hVH18

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gln Ala Tyr Gly His Tyr Met Asp Tyr Trp Gly Gln Gly Thr Leu
        100                 105                 110

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: hVH19

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
            85                  90                  95

Lys Gln Ala Tyr Gly His Tyr Met Asp Tyr Trp Gly Gln Gly Thr Ser
        100                 105                 110

Val Thr Val Ser Ser
        115

<210> SEQ ID NO 49

<211> LENGTH: 117
<212> TYPE: PRT
<213> ORGANISM: Artificial Sequence
<220> FEATURE:
<223> OTHER INFORMATION: hVH20

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 50
<211> LENGTH: 117
<212> TYPE: PRT
<213> ORGANISM: Artificial Sequence
<220> FEATURE:
<223> OTHER INFORMATION: hVH21

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ala Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 51
<211> LENGTH: 117
<212> TYPE: PRT
<213> ORGANISM: Artificial Sequence
<220> FEATURE:
<223> OTHER INFORMATION: hVH22

<400> SEQUENCE: 51

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Val
        35                  40                  45

Ser Val Ile Trp Arg Gly Gly Ser Thr Asp Tyr Ser Ala Ala Phe Met
50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 52
<211> LENGTH: 117
<212> TYPE: PRT
<213> ORGANISM: Artificial Sequence
<220> FEATURE:
<223> OTHER INFORMATION: hVH23

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
50                  55                  60

Ser Arg Phe Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 53
<211> LENGTH: 117
<212> TYPE: PRT
<213> ORGANISM: Artificial Sequence
<220> FEATURE:
<223> OTHER INFORMATION: hVH24

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
50                  55                  60

Ser Arg Leu Thr Ile Ser Arg Asp Asn Ser Lys Asn Thr Val Tyr Phe
65                  70                  75                  80

```
Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 54
<211> LENGTH: 117
<212> TYPE: PRT
<213> ORGANISM: Artificial Sequence
<220> FEATURE:
<223> OTHER INFORMATION: hVH25

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Leu Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 55
<211> LENGTH: 117
<212> TYPE: PRT
<213> ORGANISM: Artificial Sequence
<220> FEATURE:
<223> OTHER INFORMATION: hVH26

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115
```

<210> SEQ ID NO 56
<211> LENGTH: 117
<212> TYPE: PRT
<213> ORGANISM: Artificial Sequence
<220> FEATURE:
<223> OTHER INFORMATION: hVH27

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115
```

<210> SEQ ID NO 57
<211> LENGTH: 117
<212> TYPE: PRT
<213> ORGANISM: Artificial Sequence
<220> FEATURE:
<223> OTHER INFORMATION: hVH28

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Ser
            100                 105                 110

Val Thr Val Ser Ser
        115
```

<210> SEQ ID NO 58
<211> LENGTH: 117
<212> TYPE: PRT
<213> ORGANISM: Artificial Sequence
<220> FEATURE:
<223> OTHER INFORMATION: hVH29

<400> SEQUENCE: 58

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Ser Ala Ala Phe Met
        50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Leu
            100                 105                 110

Val Thr Val Ser Ser
        115

<210> SEQ ID NO 59
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 59

Gln Val Gln Leu Lys Gln
1               5

<210> SEQ ID NO 60
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 60

Asp Val Leu Met Thr Gln
1               5

<210> SEQ ID NO 61
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 61

Asp Ile Val Met Thr Gln
1               5

<210> SEQ ID NO 62
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 62

Asp Val Leu Met Thr Arg
1               5

<210> SEQ ID NO 63
<211> LENGTH: 6
<212> TYPE: PRT
<213> ORGANISM: Artificial Sequence
```

```
<220> FEATURE:
<223> OTHER INFORMATION: Variable light chain sequence variant

<400> SEQUENCE: 63

Asp Ile Val Ile Thr Gln
1               5

<210> SEQ ID NO 64
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 64

Asp Ile Val Leu Thr Gln
1               5

<210> SEQ ID NO 65
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 65

Gln Val Gln Leu Lys Glu
1               5

<210> SEQ ID NO 66
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 66

Glu Val Gln Leu Gln Gln
1               5

<210> SEQ ID NO 67
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 67

Gln Val Gln Leu Asn Gln
1               5

<210> SEQ ID NO 68
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 68

Gln Val Gln Leu Thr Gln
1               5

<210> SEQ ID NO 69
<211> LENGTH: 112
<212> TYPE: PRT
<213> ORGANISM: Artificial Sequence
<220> FEATURE:
```

<223> OTHER INFORMATION: BT063 VL

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 70
<211> LENGTH: 117
<212> TYPE: PRT
<213> ORGANISM: Artificial Sequence
<220> FEATURE:
<223> OTHER INFORMATION: BT-063 VH

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 71
<211> LENGTH: 13
<212> TYPE: PRT
<213> ORGANISM: Artificial Sequence
<220> FEATURE:
<223> OTHER INFORMATION: BT-063 VL CDR1

<400> SEQUENCE: 71

Ser Ser Gln Asn Ile Val His Ser Asn Gly Asn Thr Tyr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: BT-063 VL CDR2

```
<400> SEQUENCE: 72

Lys Val Ser Asn Arg Phe Ser Gly Val Pro Asp Arg
1               5                   10

<210> SEQ ID NO 73
<211> LENGTH: 6
<212> TYPE: PRT
<213> ORGANISM: Artificial Sequence
<220> FEATURE:
<223> OTHER INFORMATION: BT-063 VL CDR3

<400> SEQUENCE: 73

Gly Ser His Val Pro Trp
1               5

<210> SEQ ID NO 74
<211> LENGTH: 10
<212> TYPE: PRT
<213> ORGANISM: Artificial Sequence
<220> FEATURE:
<223> OTHER INFORMATION: BT-063 VH CDR1

<400> SEQUENCE: 74

Ala Ser Gly Phe Ser Phe Ala Thr Tyr Gly
1               5                   10

<210> SEQ ID NO 75
<211> LENGTH: 16
<212> TYPE: PRT
<213> ORGANISM: Artificial Sequence
<220> FEATURE:
<223> OTHER INFORMATION: BT-063 VH CDR2

<400> SEQUENCE: 75

Ile Trp Arg Gly Gly Ser Thr Asp Tyr Ser Ala Ala Phe Met Ser Arg
1               5                   10                  15

<210> SEQ ID NO 76
<211> LENGTH: 8
<212> TYPE: PRT
<213> ORGANISM: Artificial Sequence
<220> FEATURE:
<223> OTHER INFORMATION: BT-063 VH CDR3

<400> SEQUENCE: 76

Gln Ala Tyr Gly His Tyr Met Asp
1               5
```